US006291582B1

(12) United States Patent
Dordick et al.

(10) Patent No.: US 6,291,582 B1
(45) Date of Patent: Sep. 18, 2001

(54) POLYMER-PROTEIN COMPOSITES AND METHODS FOR THEIR PREPARATION AND USE

(75) Inventors: Jonathan S. Dordick, Schenectady, NY (US); Ping Wang, Akron, OH (US); Maria Vladimir Sergeeva, San Diego, CA (US); Scott Joel Novick, Iowa City, IA (US)

(73) Assignee: Biotechnology Research & Development Corp., Peoria, IL (US)

( * ) Notice: Subject to any disclaimer, the term of this patent is extended or adjusted under 35 U.S.C. 154(b) by 0 days.

(21) Appl. No.: 09/437,495

(22) Filed: Nov. 10, 1999

Related U.S. Application Data

(63) Continuation-in-part of application No. 09/336,968, filed on Jun. 21, 1999, now abandoned, which is a continuation of application No. 08/947,747, filed on Oct. 9, 1997, now Pat. No. 5,914,367

(60) Provisional application No. 60/028,564, filed on Oct. 10, 1996.

(51) Int. Cl.[7] .......................... C08F 283/00; C08G 63/48
(52) U.S. Cl. .................. 525/54.1; 527/201; 527/202; 527/203; 530/402; 530/403; 530/812; 530/815; 530/816; 530/817; 435/177; 435/180; 435/181; 435/182
(58) Field of Search ........................ 525/54.1; 527/201, 527/202, 203; 530/402, 403, 812, 815, 816, 817; 435/177, 180, 181, 182

(56) References Cited

U.S. PATENT DOCUMENTS

| 3,985,616 | 10/1976 | Weaver et al. .......................... 195/63 |
| 4,371,612 | 2/1983 | Matsumoto et al. .................... 435/44 |
| 4,727,030 | 2/1988 | Ishimura et al. ...................... 435/182 |
| 4,978,619 | 12/1990 | Kajiwara et al. ..................... 435/182 |
| 5,482,996 | 1/1996 | Russell et al. ....................... 525/54.1 |
| 5,719,039 | 2/1998 | Dordick et al. ......................... 435/41 |
| 5,914,367 | 6/1999 | Dordick et al. ..................... 525/54.1 |

FOREIGN PATENT DOCUMENTS

WO 94/08599   4/1994   (WO).

OTHER PUBLICATIONS

Bruno et al., Macromolecules 28: 8881–8883 (1995).
Ito et al., Biotechnol. Prog. 9: 128–130 (1993).
Paradkar et al., Journal of the American Chemical Society 116: 5009–5010 (1994).
Paradkar et al., Biotechnology and Bioengineering 43(6): 529–540 (1994).
Pina et al., Biotechnology Techniques 3: 333–338 (1989).
Rich et al., Chimia 50: 428–429 (1996).
Yang et al., J. Am. Chem. Soc. 117: 4843 (1995).

*Primary Examiner*—Nathan M. Nutter
(74) *Attorney, Agent, or Firm*—Heller Ehrman White & McAuliffe

(57) ABSTRACT

A method of preparing a polymer-protein composite based upon placing a protein in solution in an organic phase via the ion-pairing of the protein with a surfactant. The polymer-protein composites are useful, for example, as highly active and stable catalysts, in for example, paints and coatings, as well as in medical application.

28 Claims, 12 Drawing Sheets

POLYMER-PROTEIN COMPOSITES AND METHODS FOR THEIR PREPARATION AND USE

This application is a continuation-in-part of U.S. Ser. No. 09/336,968, filed Jun. 21, 1999 and now abandoned, which is a continuation of U.S. Ser. No. 08/947,747, filed Oct. 9, 1997, now U.S. Pat. No. 5,914,367. Each of the above applications are hereby incorporated by reference. This application also claims priority to provisional application 60/028,564, filed Oct. 10, 1996, the entirety of which is hereby incorporated by reference.

This invention was made with Government support under Grant No. 59-3K95-3-126 awarded by the U.S. Department of Agriculture, Agricultural Research Service. The Government has certain rights in the invention.

BACKGROUND OF THE INVENTION

1. Field of the Invention

The present invention relates to methods for the preparation of protein-containing polymeric materials, such as enzyme-containing polymeric materials. The present invention also relates to protein-containing polymeric materials and use of the materials, for example, as catalytic particles, in self-cleaning/non-fouling paints and coatings, as highly active and stable biocatalysts, in chemical/biochemical sensing and in medical applications including implants and in controlled drug release, immobilization, and/or stabilization of therapeutic proteins. The present invention encompasses biotechnological inventions, including biotechnological products and processes.

2. Background

Proteins, such as enzymes, are often immobilized to a support material in practical applications of biocatalysis. Numerous technologies are available for enzyme immobilization and include adsorption to a porous or nonporous support, covalent attachment to such a support, or entrapment in a solid or gelatinous support matrix. Although these approaches have served the biotechnology industry well over the years, several drawbacks have become evident. Such drawbacks include heterogeneity of enzyme loading onto the support, leakage or desorption of the biocatalyst from the support, and inactivation of the enzyme during immobilization procedures.

One approach to avoid these problems is to generate an extremely close association between the support and the biocatalyst. For example, immobilization of enzymes in hydrophilic or water-soluble polymers via polymerization in aqueous solution has been proposed and is described in the art. Such approaches have been used to prepare enzyme-containing hydrogels and other gel-like materials. Unfortunately, most of these materials are limited by the need to use highly water-soluble monomers or hydrophilic monomers, due to the solubility of enzymes that is generally limited to water and other polar solvents. For example, U.S. Pat. No. 4,727,030 to Fumihiro et al., describes the preparation of porous polyvinyl alcohol gel containing an immobilized enzyme. U.S. Pat. No. 4,371,612 describes immobilization of an enzyme via use of cross-linked microporous acrylonitrile polymers. U.S. Pat. No. 3,985,616 describes immobilization of an enzyme with gelatinized-starch-polyacrylonitrile graft polymers.

A few techniques have also been proposed for immobilization of an enzyme in organic media. U.S. Pat. No. 5,482,996 describes a protein immobilization process via covalent bonding in organic solvents. According to this patent, there is a need to modify the enzyme chemically by a modifier to dissolve the enzyme into organic media, which can alter the activity of the enzyme. As described below, such modification is not needed in the present invention. Also, the afore-mentioned modifier must be carefully controlled to be soluble in both aqueous and organic solutions and also possess a polymerizable functional groups for polymerization purpose. A typical example is acrylated polyethylene glycol, which is difficult and expensive to prepare. Another disadvantage of this process is that such modified enzymes usually show low solubility in organic solvents, thereby limiting the enzyme loading to about 0.02% by weight in the final polymer products. See Z. Yang, D. Williams, and A. J. Russell, *J. Am. Chem. Soc.*, 1995, vol. 117, 4843. The solubilized enzyme of this process also shows lower activity as compared to the technology of the present invention. See V. M. Pardkar and J. S. Dordick, *J. Am. Chem. Soc.*, 1994, vol. 116, 5009, and C. Pina, D. Clark, H. Blanch, and I. G. Gonegani, *Biotechnology Techniques*, 1989, vol. 3, 333.

Ito et al. (*Biotechnol. Prog.* 1993, 9, 128–130) describes another method of immobilization using organic solvents. Namely, Ito describes grafting enzymes with various hydrophobic vinyl polymers (e.g., polystyrene) in organic solvents by first coupling the enzyme with azobis (4-cyanovaleric acid) (ACV) in aqueous solution, followed by polymerization in organic solvents. However, the ACV-coupled enzyme is not soluble in the organic solvent, thus the chemical incorporation between the enzyme and polymer is significantly limited. Also, the final product of this technique is an enzyme-polymer complex which is soluble in organic solvents.

Entrapment of enzymes is described in U.S. Pat. No. 4,978,619. The products of this patent have an enzyme entrapped in gaps formed in a macromolecular gel matrix that is produced by dispersing the enzyme in the form of a fine powder and thus not solubilized as in the present invention described hereinafter in an organic solvent having dissolved therein a polymerizable monomer, polymerizing the monomer thereby giving rise to a gel matrix, and displacing the organic solvent in the gel matrix with an aqueous solvent. The method of this patent generates a polymer matrix containing hetero-geneous enzyme aggregates (i.e., a cluster of enzyme molecules).

The problems and limitations of the prior art are solved, avoided and/or reduced by the invention described herein.

SUMMARY OF THE INVENTION

Accordingly, it is an object of the present invention to provide improved methods for immobilizing proteins that overcome or reduce the drawbacks of previously described immobilization techniques. For example, it is desired to provide a process that allows for any proteins, including enzymes, to be incorporated into a variety of polymers, without being limited to use of hydrophilic or water-soluble polymers.

It also is desired to provide processes that allow for the amount of protein loaded into the polymer matrix to be widely varied and controlled as needed for the desired application.

It also is an object of the invention to provide methods for immobilizing a protein that does not require covalent attachment of a modifying moiety to solubilize the protein.

It also is an object of the present invention to provide immobilized proteins that overcome or reduce the drawbacks of the immobilized proteins previously prepared in the art.

It also is an object of the present invention to provide methods of using such immobilized proteins, including enzymes.

In accordance with these and other objects, there have been provided in accordance with one aspect of the present invention, methods of preparing a polymer-protein composite that include polymerizing a monomer via addition, condensation, or ring-opening polymerization in the presence of a protein dissolved in an organic phase via the ion-pairing of the protein with a surfactant.

In accordance with another aspect of the invention, there are provided polymer-protein composites prepared by polymerizing a monomer via addition, condensation, or ring-opening polymerization in the presence of a protein dissolved in an organic phase via the ion-pairing of the protein with a surfactant.

In accordance with still another aspect of the invention, there are provided methods of preparing a polymer-protein composite comprising ion-pairing a protein in an aqueous phase with a surfactant in a first organic phase to yield a protein-surfactant ion pair; contacting the protein-surfactant ion pair with a second organic phase containing at least one selected from the group consisting of the polymer or a monomer that can be polymerized to yield the polymer; removing the second organic phase to yield a polymer-protein composite. The second organic phase can comprise the monomer, the polymer or both. The protein can be modified chemically with one or more reactive functional groups (such as vinyl groups and acrylate groups) that can form a covalent bond with the polymer. The protein can be a naturally-occurring protein, and can be an enzyme. Preferably, the polymer-protein composite obtainable by the methods comprise from about 0.05% to about 90% by weight of protein, based on the total weight of the composite. The overall invention, however, is not limited to a certain percentages of protein in the composite, which the skilled person will understand are often, but not always, approximations.

In accordance with yet another aspect of the invention, there are provided methods of preparing a polymer-protein composite that comprises (a) contacting and mixing a protein-containing aqueous solution with a surfactant in an organic solution to yield an organic phase containing an protein-surfactant ion pair, (b) separating out the organic phase that contains the ion pair from the aqueous phase that no longer contains the ion pair, (c) removing the organic solution from the organic phase of (b), (d) dissolving the ion-pair in a second organic solution, (e) contacting the dissolved ion-pair of (d) with a polymer that also is dissolved in the second organic solution to form a polymer-protein complex and (f) recovering the polymer-protein complex. The protein can be modified chemically with one or more reactive functional groups (such as vinyl groups/ acrylate groups) that can form a covalent bond with the polymer. The protein can be a naturally-occurring protein, and can be an enzyme. Preferably, the polymer-protein composite obtainable by the methods comprise from about 0.05% to about 90% by weight of protein, based on the total weight of the composite.

In accordance with a further aspect of the invention, there are provided polymer-protein composites comprising a protein incorporated in a polymer, wherein the polymer-protein composite comprises from about 0.05 to 90% by weight of protein, based on the total weight of the composite, wherein the polymer-protein composite is obtainable by any of the above methods. The polymer-protein composite can include proteins covalently bound to the polymers. In addition or as an alternative, the proteins can be entrapped in the polymer, but not covalently bound to the polymer.

In accordance with yet a further aspect of the invention, there are provided composites containing two or more different types of proteins (such as two different enzymes and/or ligands/receptors) and two or more types of polymers (including homogeneous polymers and heterogeneous polymers, such as co-polymers and block co-polymers). If desired or necessary, the process methodologies to make composites in accordance with applicants' inventions can employ two or more surfactants and solvents.

In accordance with still a further aspect of the invention, there are provided paints, coatings/films (including biocatalytic and antifoaling coatings/films), catalytic particles, catalyst packings, bioreactive membranes and various medical applications including such polymer-protein composites.

Further objects, features, aspects, uses and advantages of the present invention will become apparent from the detailed description of preferred embodiments that follows.

DETAILED DESCRIPTION OF PREFERRED EMBODIMENTS

Figure 1:
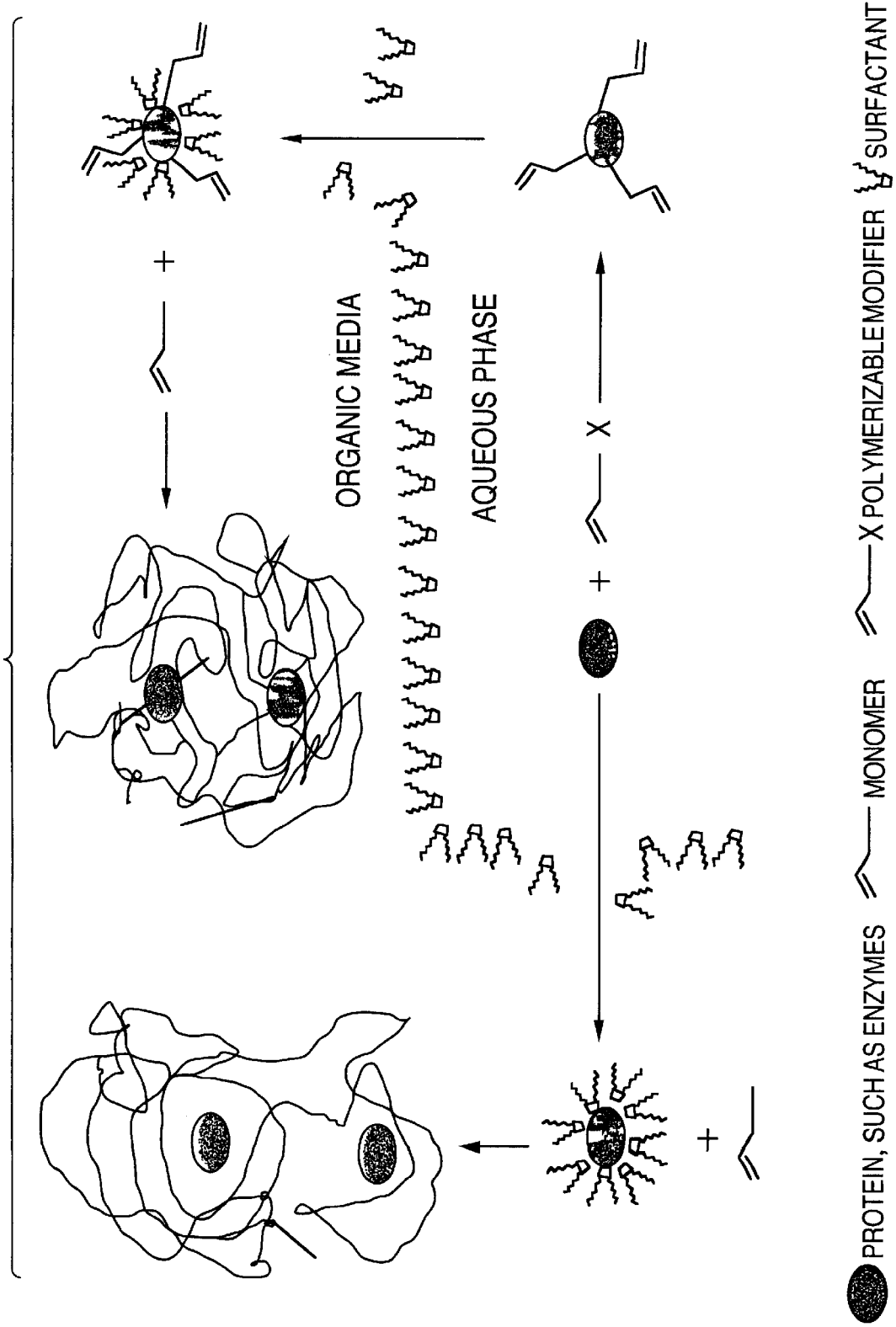
FIG. 1 is a schematic diagram that shows how proteins, such as enzymes, are incorporated into polymers according to the present invention.

It has been discovered that proteins, such as enzymes, can be dissolved in organic solvents via the ion-pairing of the protein with a surfactant. As understood by those in the art in view of the teachings contained herein, by ion-pairing is meant that the protein and surfactant have portions with opposite charges which bond together to form an ion-paired complex. For example, a protein with a positive charge ionic bonds to the negative charged portion on a surfactant to thereby form an ion-paired protein surfactant complex. See U.S. patent application Ser. No. 08/457,758 filed Jun. 1, 1995, the disclosure which is hereby incorporated by reference in its entirety. The protein-surfactant complex is highly soluble in a variety of organic solvents. Moreover, there is no need to extensively derivatize the protein with amphiphilic polymers, such as polyethylene glycol and the like, to enable the protein to dissolve in the organic solvent, as in U.S. Pat. No. 5,482,996. The ion-paired protein-surfactant complexes are extremely soluble and active in organic solvents. For example, transesterification activity of the enzyme subtilisin Carlsberg in isooctane for transesterification is essentially identical to the activity of the enzyme in water. Thus, the enzyme-surfactant, ion-paired complexes demonstrate native-like activity in organic solvents.

The present invention takes advantage of such active and soluble protein forms in organic solvents to generate biocatalytic plastics. Because the protein is soluble in organic solvents, it can be incorporated, either covalently or via entrapment into a wide variety of plastic materials, including hydrophobic polymers (such as polystyrene, poly(methyl) methacrylate, or polyvinyl chloride) or amphiphilic polymers, such as polyethylene glycol.

Besides or in addition to enzymes, any other proteins, such as hormones, toxins, antibodies, antigens, lectins, structural proteins, signal proteins, transport proteins, receptors, blood factors, and others can be used in the present invention. While the detailed description often focuses on enzymes, any desired proteins can be used.

As discussed earlier, most prior immobilization techniques were only feasible with water-soluble (hydrophilic and amphiphilic) polymers. The present invention substantially broadens the range of protein supporting materials (e.g., polymers) that can be used, thereby allowing much more freedom in choosing materials that possess desirable characteristics such as mechanical strength, thermal and chemical stability, steric properties, including, accessibility and flexibility, and hydrophobicity/hydrophilicity, and loading capacity to meet specific requirements in both aqueous and non-aqueous applications. Thus, a variety of conventional plastic building blocks and the like can be utilized to generate a wide diversity of biocatalytic plastics, paints, coatings, substrates, and other materials.

The polymer-protein composites of the present invention can be used in applications where other polymer-protein composites are currently being used or being investigated today. As understood by those in the art, the uses of the inventive polymer-protein matrix depend on what kind of protein is incorporated to the polymer. For example, antibodies and other therapeutic proteins may be used as implants, injections or in oral medicine; and enzymes may be used where large scale of biocatalytic processing is involved, such as high performance catalyst for peptide synthesis, chemical and food processing.

The polymer-protein composites can be used in paints. For example, the composites in a solid particle form, can be mixed and ground with pigment and other conventional additives for various paints used, for example, for automobile, building, medical devices, and furniture. Depending on the function of the protein used, the paint may have desired properties such as easy-cleanability, antibacterial affect, and/or self-degradability.

The polymer-protein composites can also be used in coatings. The coatings can be formed directly via the in-situ polymerization or like a paint such that additives are added to the composite to form a desired coating. The coatings can be used in various applications such as in coatings to increase the biocompatibility of medical materials used in contact or inside human bodies or other things containing living material; as coatings on electrodes for chemical probes such as glucose sensors; as coatings on bioreactors and/or packed materials used for starch degradation, milk processing, waste water treatment, and the like.

The polymer-protein composite can also be used as catalyst particles, particularly for use in packed-bed reactors. The packed-bed reactors can be those used for glucose isomerization, selective penicillin hydrolysis, selective reactive separation of racemic mixtures of amino acids, food and beverage processing, and other processes.

The polymer-protein composite can be used in various medical applications, such as in catalyst for drug processing such as peptide synthesis; racemic biochemical separation; controlled drug release via biodegradable linkages between the protein drug and the polymer; highly bio-compatible biomaterials; and other medical uses.

In accordance with one aspect of the present invention, the solubilized protein-surfactant, ion-paired proteins are mixed with monomer and polymerization can be carried out in situ. The organic phase may include any desired solvents. Also, the organic phase can actually consist of, consist essentially of, or comprise the polymerizable monomer. Therefore, additional monomer need not be added to the solubilized protein-surfactant, if the solubilization is accomplished with a polymerizable monomer. Any type of monomers or mixtures of monomers can be used. The polymerization can be carried out using techniques known in the art, in view of the teachings contained herein, such as addition, condensation, or ring-opening polymerization.

In one aspect of the invention, the solubilized protein-surfactant, ion-paired enzymes are mixed with a vinyl monomer and optionally a crosslinker in an organic solvent and polymerization is carried out in situ.

A crosslinker that crosslinks the modified or unmodified proteins and/or polymers may be used if desired, but is not required. The product of the present invention includes protein-containing solid materials. It is often possible to form such a solid material without using a crosslinker. For example, in the polymerization of poly(methyl) methacrylate, the crosslinker trimethacrylate (TMA) may be used. However, although the product may come out with lower yield and/or mechanical strength, a solid polymer material can also be formed under the same or similar conditions without the use of the crosslinker.

The present products can also be made into flowable materials, such as gels. Also, the products can be made into contact lenses.

A crosslinker may be added to help the formation of a solid phase from the reaction mixture, or to adjust the physical characteristics, such as mechanical strength, thermal and chemical stabilities, etc. of the final product.

One or more proteins, one or more surfactants, optionally one or more organic solvents, one or more monomers and/or polymers, and optionally one or more crosslinkers may be used. Any desired protein, surfactant, solvent, monomer, and crosslinker can be used, so long as an ion-paired protein-surfactant complex as described above is prepared. For example, a composite according to the invention may contain two or more proteins and two or more polymers. The ion-pairing can be brought about by using two or more surfactants. Those skilled in the art are aware of materials from these classes and can select them based on the general knowledge art and the present specification.

Examples of useful proteins, surfactants, and solvents and their proportions to make the protein-surfactant ion-paired protein are described in previously mentioned copending application Ser. No. 08/457,758. Also, U.S. Pat. No. 5,482,996, describes proteins, monomers, and solvents than can be used with the present invention.

The enzymes are useful as the proteins may be selected from any proteins with biochemical activities, such as chymotrypsin, trypsin, subtilisin, horseradish peroxidase (HRP), soybean peroxidase (SBP), and glucose oxidase. A preferred enzyme is u-chymotrypsin. As mentioned above, proteins other than enzymes also are useful.

The organic solvent which may optionally make up the organic phase can be selected from any desired polar or non-polar solvent which dissolves the protein-surfactant complex. As mentioned earlier, the organic phase can consist of or consist essentially of or comprise a polymerizable monomer and hence the organic phase need not include additional organic solvent. The polarity of organic solvents may be scaled by $\delta$, solubility parameter (Thomas H. Lowry, Kathleen Schueller Richardson, Mechanism and Theory in Organic Chemistry, Harper & Row, NY 1981.). Accordingly, non-polar solvents have lower $\delta$ value, such as hexane (7.3), toluene (8.9), ethylacetate (9.1), tetrahydrofuran (9.1), and the like. Polar solvents, on the other hand, are those having higher $\delta$, such as tert-amyl alcohol (10.9), acetone (9.9), DMSO (12.0), methanol (14.5). The $\delta$ values in parenthesis are in units of $(cal/cm^3)^{1/2}$, from Polymer Handbook, by J. Brandrup, E. H. Immergut. Wiley, 1989.

The solvents of the present invention may include any single solvent or mixture of solvents having a $\delta$ value of lower than about 23.4, the value of water. Generally, the $\delta$ should be above about 3. Especially useful solvents include those mentioned above as well as isooctane, octane, hexane, toluene, ethyl acetate, acetonitrile, and tetrahydrofuran.

The surfactant is selected from any desired surfactant that will ion-pair with the selected protein. The surfactants may be anionic or cationic. Useful anionic surfactants include bis(2-ethylhexyl) sodium sulfosuccinate (AOT), bis(2-ethylhexyl) phosphate (NaDEHP), tauroglycocholate, and sodium lauryl sulfate. A useful cationic surfactant is tetradecyltrimethyl-ammonium bromide (TTAB). A particularly useful surfactant is AOT.

The polymerizable monomer is selected from any desired polymerizable monomer. Such monomers are well known and readily obtained by those in the field of polymers. Monomers may be classified according to the way they are polymerized. The polymerization reaction can be classified into three primary categories: condensation, addition, and ring-opening polymerization. (Allcock and Lampe, *Contemporary Polymer Chemistry*, 2nd ed, Prentice-Hall, 1990). The monomer may fall into any of these categories. Examples of useful condensation monomers include carbonates anhydrides, amides, and the like. Examples of useful addition monomers include styrene, vinyl acetate, acrylonitrile, acrylates, and the like. Examples of useful ring opening monomers include furans, oxetanes, epoxides, lactones, and the like. Preferred monomers include vinyl monomers that are used in addition polymerization such as methyl methacrylate, vinyl acetate, ethyl vinyl ether, and styrene. Any type of polymerization can be used to make the composites of the present invention, in accordance with aspects of the present invention.

The optional crosslinker may be selected from any component that functions to crosslink the polymer-protein composite. The crosslinker may crosslink the polymer backbone and/or the protein, especially if the protein is modified with a functional group as described hereinafter. Useful crosslinkers include substances that possess more than one functional group which can undergo polymerization reactions with the monomers or the optional functional group of the protein. Examples of useful crosslinkers include trimethylopropane trimethacrylate (TMA), and divinyl benzene (DVB).

Unmodified, native proteins, such as enzymes, can be used in the process. Altered or modified proteins, including altered or modified enzymes, also can be used according to the invention. For example, reactive functional groups may be chemically attached to the protein molecules, generally prior to the solubilization process. Modifiers for attachment to proteins include organic compounds that can be attached chemically to the protein molecules, and possess one or more polymerizable functional groups such as a vinyl group that can undergo polymerization reaction with other monomers. These functional groups can participate in the polymerization reaction, thereby leading to the covalent attachment of the protein to the resultant copolymers. Examples of useful functional groups include polymerizable functional group, such as vinyl groups, preferably acrylates. Examples include acryloyl chloride, the groups used in U.S. Pat. No. 5,482,996 discussed previously, such as acrylated polyethylene glycol, and the like.

If an unmodified, non-reactive native enzyme or other unmodified protein is used, the protein will likely become entrapped in the polymeric matrices, rather than covalently bonded to the vinyl monomers.

For aspects employing contemporaneous polymerization, the polymerization can be accomplished in any desired manner, such as via free radical, ionic, or condensation polymerization mechanisms. The polymerization techniques known in the art can be used in the present process. The polymerization can be bulk, solution, emulsion, or suspension polymerization.

The polymer-protein composites made according to the present invention are unique in several ways. First, a wide variety of proteins, such as enzymes, can be used. In particular, both unmodified native proteins and/or proteins derivatized with a simple functional group, such as an acrylate group, such as those having a molecular weight of less than 1,000 or less than 100, can be used. For example, the modification disclosed in U.S. Pat. No. 5,482,996 is not required. It is often useful to use unmodified proteins, such as enzymes, to reduce the denaturation of the protein that results from such modification.

Second, proteins, such as enzymes, can be used that are extremely active and stable in a variety of organic solvents. Thus, highly active enzymes can be incorporated into the plastic material. The ion-pairing of the protein with the surfactant provides increased solubility of the protein in a wide variety of organic solvents and monomers.

Third, the method is general such that a wide variety of proteins can be solubilized in organic phases solvents via a non-covalent mechanism. The method also provides protection of the proteins during the solubilization and in situ polymerization.

Fourth, the broad group of polymers available to the polymer chemists can be used to generate a whole host of functional biocatalytic materials. The invention is not limited to the use of hydrophilic polymers as in the previously described aqueous-based technology. Proteins can be homogeneously or heterogeneously incorporated into various general purpose plastics. The entrapment process of the present invention can result in a protein homogeneously entrapped (even on a molecular level) into a polymer. Also, composites can be formed that are not soluble in either aqueous or organic solutions. Thus, molded plastics, coatings, paints, slabs, and the like formed from any desired polymer can be made that contain proteins.

Fifth, incorporation of the protein into the polymer can be controlled as desired, thus high protein incorporation can be obtained. Specifically, in the process of the present invention, a protein, such as an enzyme, can be loaded up to the theoretical limits. The theoretical limitation on protein loading is the weight ratio between protein and modifier (e.g., α-chymo-trypsin/acryloyl chloride pair has a weight ratio of 25,000/91, i.e., enzyme loading could be up to a 99.6% by wt.). Therefore, according to the present invention, protein loading from about 0.001 up to about 99.9 % is possible. Generally, in the present invention, protein loading is between about 0.05% and about 90%, more preferably, about 0.1% to about 50%, more preferably about 1% to about 20% by weight of the polymer-protein composite. The method of U.S. Patent 5,482,996 achieves products with enzyme loading of up to only about 0.02% (See Yang and Russell, et al., *J. Am. Chem. Soc.*, 1995, 117, 4843.)). Thus, highly active plastics containing any desired amount of protein can be obtained according to the present invention.

FIG. 1 is a schematic diagram that illustrates how proteins (specifically enzymes) are incorporated into the polymers. Two approaches are evident from FIG. 1. In one (left side of FIG. 1), the enzyme is simply extracted into the organic phase by ion-pairing with a surfactant, such as Aerosol OT (AOT, an anionic surfactant) followed by polymerization of vinyl monomers around the organic solvent soluble enzyme to entrap the enzyme.

In the second case (right side of FIG. 1), the enzyme is first chemically derivatized with functionalities, such as acrylates, which are then utilized in a copolymerization reaction with vinyl monomers to give a covalently incorporated enzyme in a plastic matrix.

A general procedure for forming the composites of the invention is outlined below. The procedure uses enzymes as an exemplary protein, but any desired protein can be used. Attention is also directed to previously mentioned copending application Ser. No. 08/457,758 filed Jun. 1, 1995, for further methods for forming the protein dissolved in an organic solvent via the ion-pairing of the enzyme with a surfactant.

General Procedure (1) Enzyme Aqueous Solution Preparation: Enzyme is dissolved in a buffered solution. The buffer solution is used to maintain the pH value of the aqueous solution at a desired value. The pH value can be adjusted to satisfy the requirements for the particular chemical reaction and solubilization process used. The enzyme can be in its native state, or modified with a polymerizable functional group, such as a vinyl group. A preferred functional group is an acrylate group from acryloyl chloride. Protein molecules will be positively charged if the pH value of buffer solution is lower than the protein's pI, and will be negatively charged if higher. The pI of a protein is the pH value at which the protein is isoelectric. Depending on whether an anionic or a cationic surfactant is used, by adjusting the pH value of the buffer to alter the polarity of the enzyme charge, ion-pairing between the surfactant and protein is ensured.

(2) Surfactant Organic Solution Preparation: A surfactant, such as AOT, is dissolved into an organic solvent to a desired concentration. The surfactant concentration is preferably adjusted to achieve the maximum extraction of enzyme in step (3). The concentration can be up to the solubility limitation of the surfactant in any particular solvent. An optimal concentration may exist in terms of maximum enzyme extraction for a specific system. The optimal concentration is determined experimentally for the particular system to be used.

(3) Enzyme solubilization into non-aqueous media: The solution prepared in operation (2) is added to that of (1). For example, a volume ratio between organic and aqueous phase may range from about 0.1:1 to 10:1. Adequate amount of additives, such as $CaCl_2$ and 1-propanol and 2-propanol, may be added to the mixture. Additives are added to achieve higher protein extraction ratio and easier phase separation. The addition of inorganic salts, such as $CaCl_2$ and KCl, is believed to make the phase separation more complete and faster. The hydrophilic small organic molecules such as 1-propanol and 2-propanol, may facilitate the contact between the surfactant and the enzyme, and lead to better extraction. While these exemplary additives will generally work well, it is possible for the skilled person to determine other additives for each particular enzyme, buffer solution, surfactant, and organic solvent, in view of the teachings contained herein.

The mixture is then mixed by stirring, or shaking, or other mixing techniques. The mixture then forms two phases by keeping the mixture still or using other phase separation techniques, such as centrifugation. Each of these operations is typically performed within a few minutes. If the aqueous and organic solutions are kept unmixed but placed in contact, protein can also be extracted, but the process may require a longer time period, such as hours or days, to achieve a similar protein extraction ratio. The enzyme containing organic phase is optionally dried (partially or totally) to remove the volatile components in the solution, for example, by vacuum or purging clean gas, such as $N_2$. Drying, however, is not required. The dried enzyme-surfactant complex can then be redissolved into an organic solvent, which may be different from or the same as that used in the solubilization step. Also, the dried enzyme-surfactant complex may be dissolved into a pure monomer like methyl methacrylate, which then acts as a solvent. In such a case, no other solvent is required.

(4) Monomer solution: A desired amount of monomer sufficient to undergo polymerization and optionally a cross-linker is added to the enzyme-containing organic solvent. The monomers can be added in pure form or as a solution in an organic solvent. Any monomers or mixtures of monomers can be used. Note if monomer is used as a solvent in step (2), (3) or (4) additional monomer need not be added. That is, step (4) may be optional in such cases. Also up to 5% by volume of water may be added to increase the stability of the enzyme and/or the solubility of the monomer. Other additives may also be used in the solution for purposes such as adjusting the physical/chemical properties of the final product, altering the solubility and/or reactivity of the other components in the solution, and the like.

(5) Polymerization: The techniques known to those in the art to polymerize monomers are useful in the present invention. The polymerization can be initiated by conventional methods such as by adding a catalyst or an initiator, or supplying heating, light or electronic beam, radiation, or a combination of the above. Initiators may be chosen as understood by those in the art according to the polymerization systems concerned. Examples include redox agents and azo compounds for free radical polymerization, and aluminum alkyls and organic radical anions for ionic polymerization.

(6) Purification: The resultant polymer may be purified as desired, such as washed with an organic solvent to remove any small molecules, and then by water to remove any free enzyme molecules. The washed polymer may then be dried under vacuum.

The above procedure, due to use of a functionalized enzyme, results in the enzyme being covalently bonded to the polymer matrix, that is, a copolymer between the enzyme and vinyl monomers is formed. An alternative procedure can be used that involves entrapment of the enzyme within the polymer matrix rather than copolymerization and covalent incorporation. This involves omitting the chemical modification of step (1), but the enzyme is still dissolved into a buffer solution in order to be solubilized into the organic solvent by the surfactant, and continuing with the organic solvent-soluble enzyme preparation.

The polymerization condition, such as temperature, time, and pressure can be selected as desired. For example, polymerization can be conducted at room or lower temperature, since higher temperature may cause much more denaturing of the enzyme. The polymerization can be typically done within 24 hours or a few days. Elevated or reduced pressure can be used, but normal pressure can also be advantageously used, thereby simplifying the procedure.

(7) Polymers: Of course, in methodologies that employ only already-formed polymers, the polymerization can be omitted because the necessary polymer has already formed. Reactions may still be necessary, however, in situations where cross-linking is desired and/or the protein (such as an enzyme) is to be covalently bound to the polymer.

The present invention is illustrated by the following examples. The examples are illustrative and do not limit the scope of the invention in any manner.

EXAMPLE I

Vinyl-type plastics containing covalently bound α-chymotrypsin.

Acryloyl chloride was added at 0° C. to a 0.2 M pH 8 phosphate buffer solution containing 1.5 mg/ml of α-chymotrypsin. The total amount of acryloyl chloride was applied at a ratio of 100 moles per mole of enzyme, and was added within 30 min. The pH value was adjusted to pH 8.0 during this process with diluted KOH solution. The enzyme was then desalted (to remove unreacted acryloyl chloride and any formed free acrylic acid, as well as the buffer salts) by passing through a Sephadex gel column (size 100–300 μm) with 10 mM pH 7.8 Bis-Tris propane buffer as the mobile phase. The desalted enzyme solution was collected for the solubilization step.

To the salt free enzyme solution, 2 mM $CaCl_2$ was added along with 1% (v/v) of 1-propanol or 2-propanol. This solution was then mixed with an isooctane solution containing 2 mM AOT in a volume ratio of 1:1, and stirred at 250 rpm for 3 min. The organic phase was removed following phase separation and dried by purging nitrogen. Then, a certain amount of anhydrous isooctane was added to make a solution containing enzyme at a concentration of about 1 to 10 mg/ml. Enzyme concentration (for example chymotrypsin) of up to 250 mg/ml can be used. Other organic solvents can be used at this point including octane, hexane, toluene, ethyl acetate, and/or tetrahydrofuran, among others.

To 2 ml of the enzyme solution in isooctane, 0.5 ml of vinyl monomer was added. The monomer was chosen from methyl methacrylate, vinyl acetate, ethyl vinyl ether, and/or styrene. A crosslinker, either trimethylolpropane trimethacrylate or divinyl benzene, was added at a ratio of about 20% (v/v) of the monomer. An amount of 5–20% of crosslinker can be used. Then, 2,2'-azobis-(2,4-dimethylvaleronitrile) was added as initiator (0.2% of monomer in terms of molar ratio). The solution was mixed well, purged by nitrogen for 45 seconds, and polymerization initiated by shining 365 nm UV light on the solution. Polymerization was allowed to continue for 24 hours.

The resulting polymer was washed extensively by hexane, dried under vacuum, then washed by water until no observable protein fell out from the polymer. The final product was dried totally under vacuum and stored at 4° C. Analysis showed that in the case of chymotrypsin, more than 60% of the enzyme remains active right after polymerization, and up to 30% of the originally added enzyme is available for catalytic reactions in the final product, as determined via elemental analysis and active site titration experiments. Measurements also showed that the activity of the immobilized enzyme is about 10% of the native enzyme for hydrolysis reactions in water, and up to more than 200 times higher than the native enzyme in toluene in terms of transesterification activity.

EXAMPLE II

Plastics with entrapped a-chymotrypsin

Without chemical modification, salt free enzyme was dissolved into 10 mM pH 7.8 Bis-Tris buffer, and the same solubilization and polymerization procedure described in Example I was carried out.

EXAMPLE III

Plastics containing covalently bound subtilisin Carlsberg

The same procedure of example I is followed, but the enzyme subtilisin Carlsberg replaces α-chymotrypsin as the protein.

Results

The Results of Examples 1–3 are discussed below with reference to the FIGS. 2–6. The results demonstrate the value of the technique of the invention for developing biocatalytic plastics. The solvents of FIGS. 2–6 such as hexane, toluene and t-AA, used for catalytic reactions are fresh solvents, not the one used during the polymerization reaction.

Figure 2:
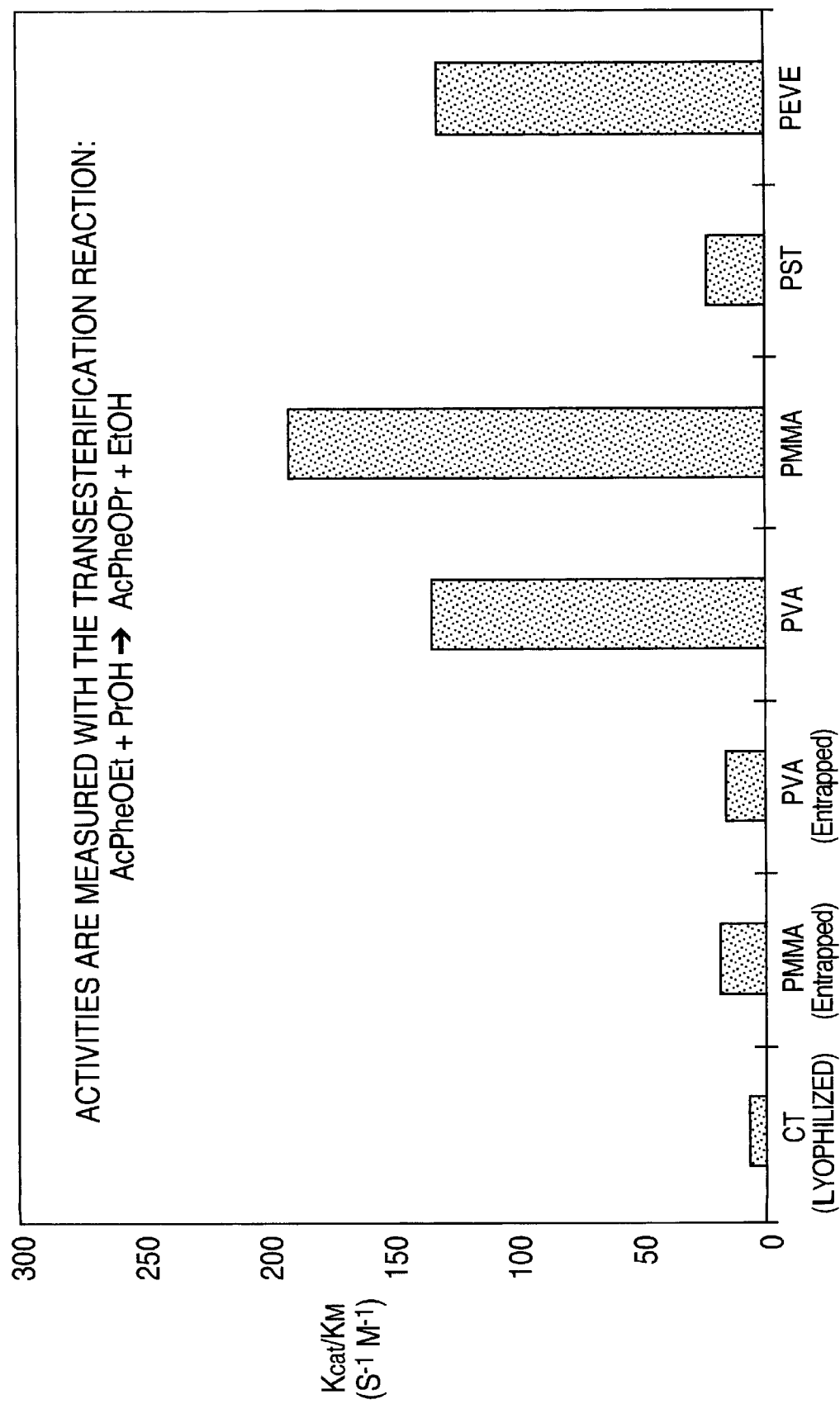
FIG. 2 is a bar graph that demonstrates the activity of α-chymotrypsin-containing polymers in hexane prepared according to the invention.

FIG. 2 graphically demonstrates the activity of α-chymotrypsin incorporated into different polymers in hexane according to Examples 1 and 2 of the present invention. The values of $k_{cat}/K_M$ are given for the enzyme entrapped (Example II) or covalently (Example I) incorporated into different plastics. In the FIGS. 2 and 3, the entrapped examples are indicated as such, whereas the other examples are covalent incorporation. Comparison is made to the free suspended enzyme in hexane (CT). Legend: PMMA=poly (methyl methacrylate); PVA=poly(vinyl acetate); PST=poly (styrene); and PEVE=poly(ethyl vinyl ether). It can be seen that all examples of the invention are more active than the free enzyme and that the covalently incorporated enzyme in PMMA is about 25-fold more active than the freely suspended enzyme in hexane.

Figure 3:
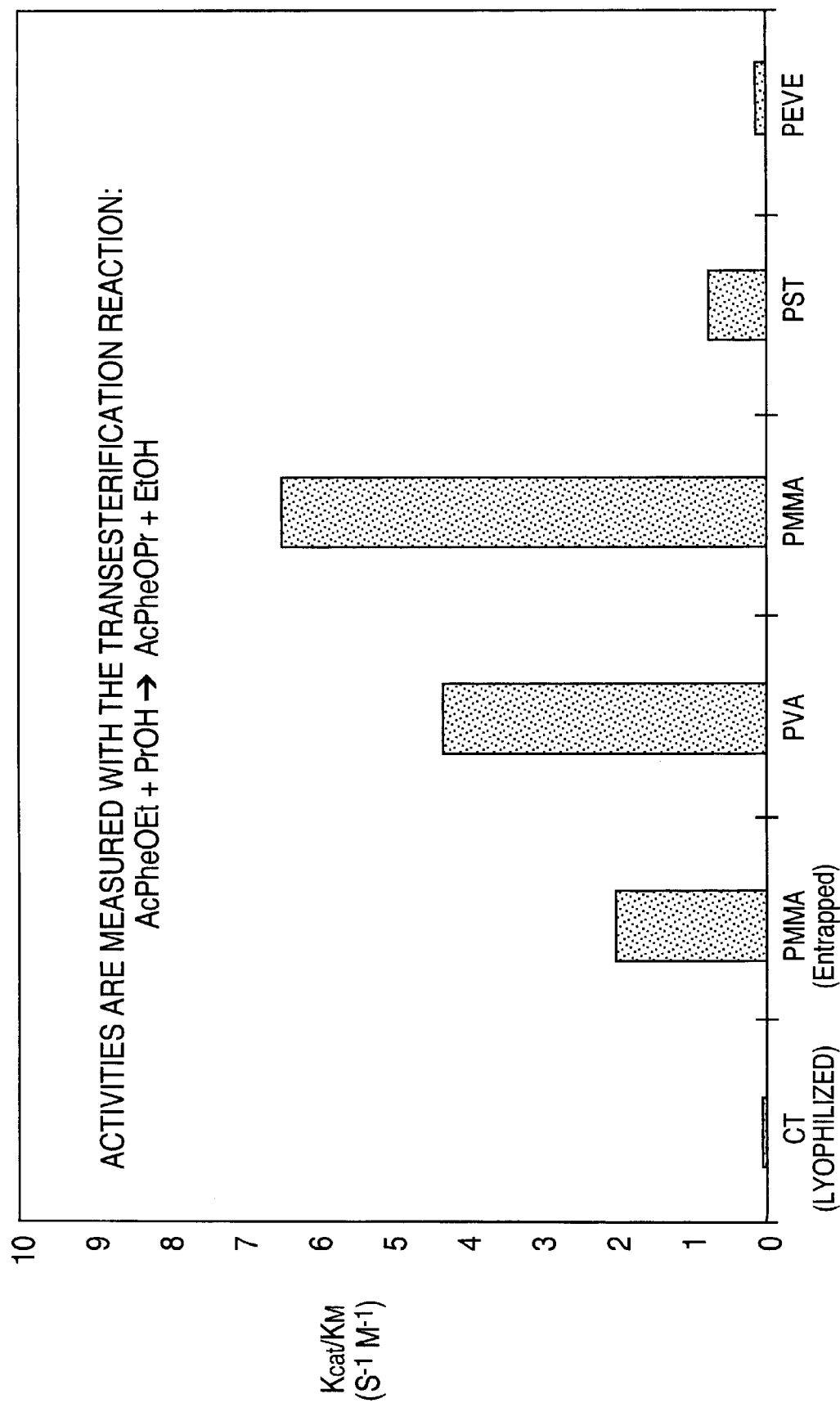
FIG. 3 is a bar graph that demonstrates the activity of α-chymotrypsin-containing polymers in toluene prepared according to the invention.

FIG. 3 demonstrates the activity of α-chymotrypsin incorporated into different polymers in toluene according to Examples 1 and 2. As seen from FIG. 3, all examples according to the invention are more active than the free enzyme and that incorporation into PMMA and PVA gives particularly good activity—215 fold and 142 fold higher than the native enzyme by PMMA and PVA, respectively.

Figure 4:
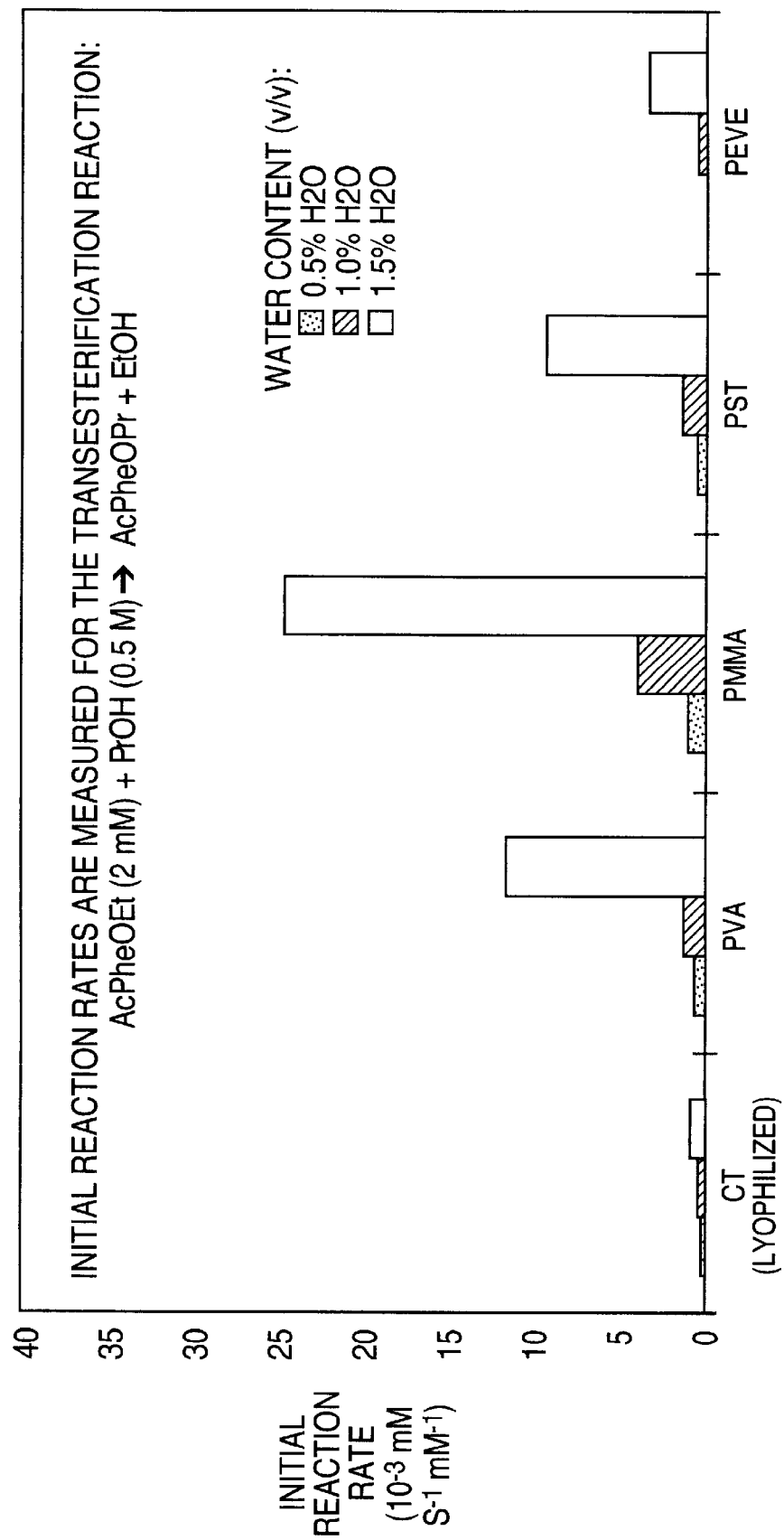
FIG. 4 is a bar graph that demonstrates the activity of α-chymotrypsin-containing polymers in the polar solvent tert-amyl alcohol prepared according to the invention.

FIG. 4 demonstrates the activity of α-chymotrypsin incorporated into different polymers in the polar solvent tert-amyl alcohol (t-AA) with small amounts of water. This organic solvent is much more polar and hydrophilic than toluene or hexane. The free enzyme is poorly reactive in tert-amyl alcohol; however, the covalently incorporated enzyme in PMMA and PVA, particularly, is reactive. Addition of water greatly stimulates the biocatalytic plastic, such that addition of 1.5%, v/v, water increases the activity over the dry suspended enzyme well over 26-fold. Water was added to the pure solvent (t-AA) prior to the addition of any substrates and enzyme/polymer composites.

Water, for example, greater than 0.03% v/v, for example, from about 0.03% to about 2.5% v/v, can be used to increase activity of the present polymer-protein composites, to increase efficiency of the catalyst, to increase yield of the products, and/or to increase half life of the catalyst. See PCT/US96/08726, filed Jun. 3, 1996, incorporated in its entirety by reference herein.

Figure 5:
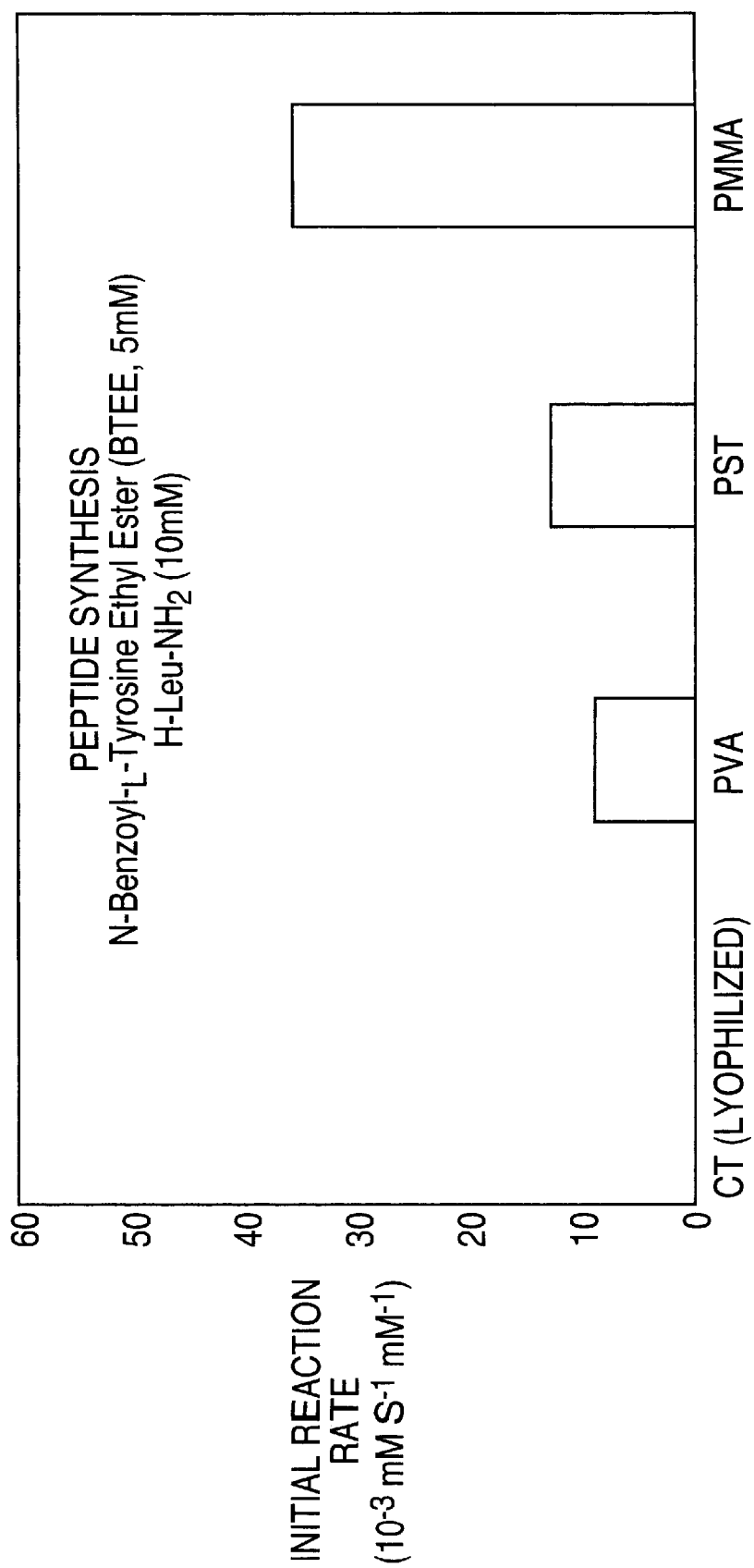
FIG. 5 is a bar graph that demonstrates the activity of α-chymotrypsin-containing polymers in a mixture of isooctane/THF (70/30 v/v) prepared according to the invention.

FIG. 5 demonstrates the activity of immobilized α-chymotrypsin for peptide synthesis in a mixture of isooctane/THF. This represents the coupling of N-Benzoyl-$_L$-Tyrosine Ethyl Ester with L-Leu-NH$_2$ to give the dipeptide in isooctane-THF (7:3) using α-chymotrypsin incorporated into different polymers. The PMMA shows an initial reaction rate of about 500 times higher than that of free enzyme suspension.

Figure 6:
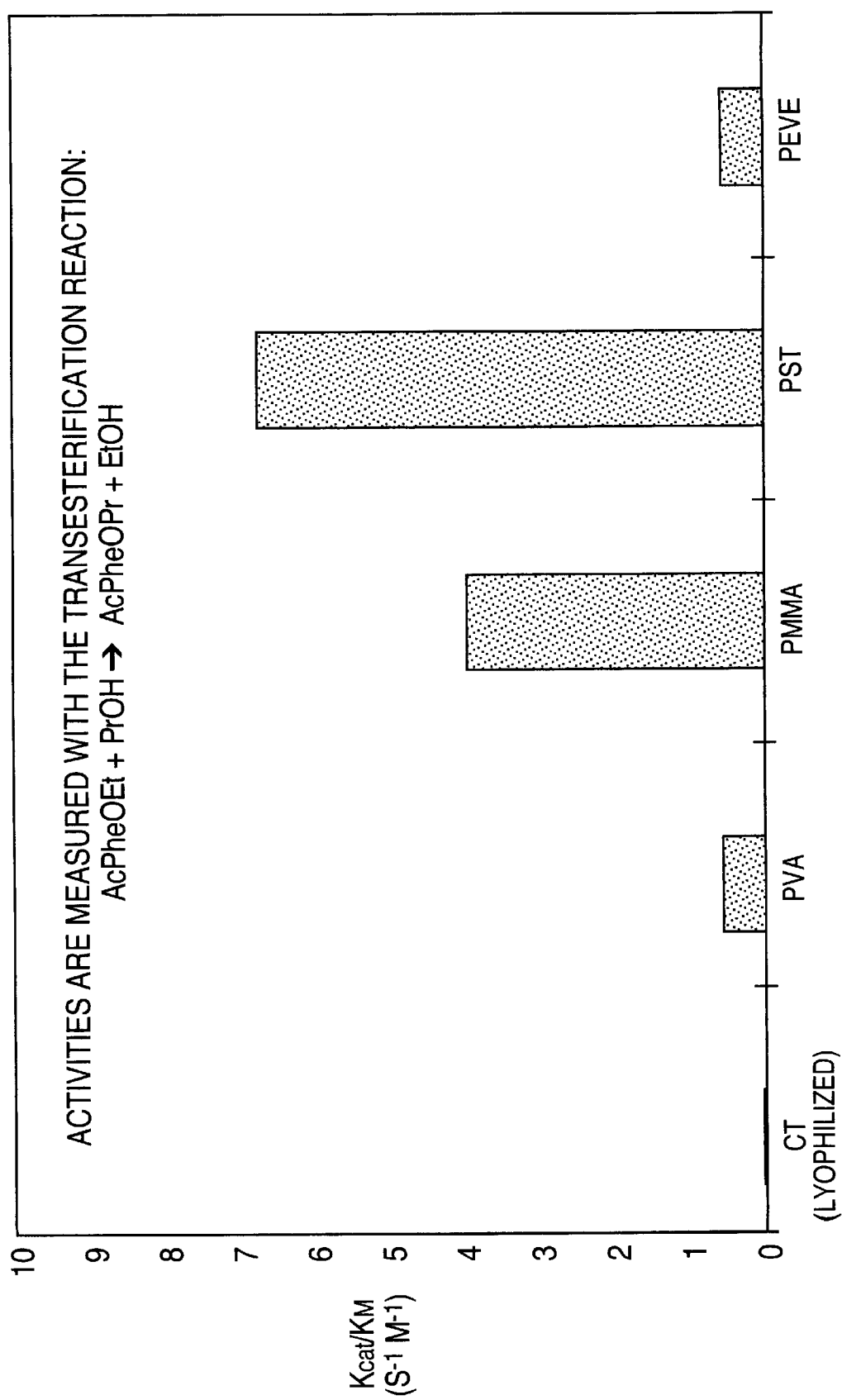
FIG. 6 is a bar graph that demonstrates the activity of subtilisin Carlsberg-containing polymers in hexane prepared according to the invention.

FIG. 6 demonstrates the activity of subtilisin Carlsberg-containing polymers, as prepared from Example III, in hexane. The subtilisin-containing polymers also show higher activity than that of free subtilisin suspension. PST shows an activity of more than 300 times higher than that of free enzyme.

Figure 7:
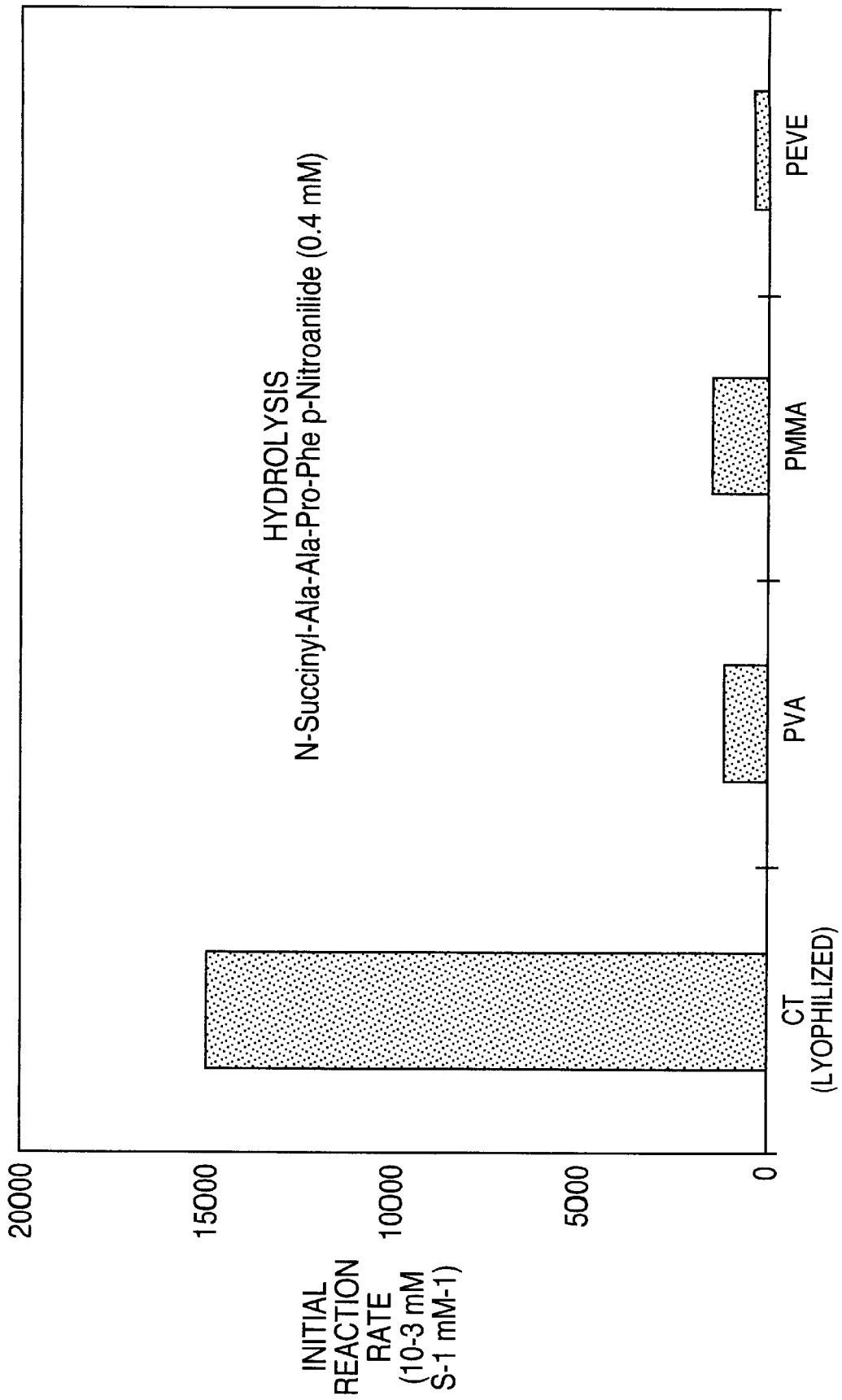
FIG. 7 is a bar graph that demonstrates the activity in terms of initial reaction rate of α-chymotrypsin-containing containing polymers in a pH 7.8 aqueous solution prepared according to the present invention.

FIG. 7 demonstrates the activity of chymotrypsin-containing polymers of Example 1 in aqueous solutions. The observed activities (in terms of initial reaction rates) for the polymers are up to 10% of that for the free enzyme. Enzyme activity in aqueous solutions is expected to decrease upon the immobilization due to the introduction of the limitation from the polymer matrices on the contact between the enzyme and substrates. The advantages for using immobilized enzymes in aqueous solutions for biocatalysis involve simplified purification of the product and recovery of the enzyme catalyst, flexible reactor design, and improved enzyme stability, among others. The data shown here demonstrates that the current technology also leads to products suitable for applications in aqueous solution.

The results shown in FIGS. 2–7 demonstrate that the enzymes remains highly stable and active in the polymer matrix, and can be used in organic or aqueous media.

An example that uses ring-opening polymerization follows the procedure as in Example I, except:
(a) epichlorohydrin is used as the modifier instead of acryloyl chloride
(b) following solubilization and drying of the modified u-chymotrypsin, chloroform (rather than isooctane) is added to re-dissolve the enzyme-AOT complex.
(c) to 1 ml of the solution formed in step (b), 0.5 ml of propylene oxide and 0.5 ml of bisphenol A is added rather than a vinyl monomer. A small amount of amines (for example 10% of the weight of the monomers) may be added as a cross link reagent, and strontium carbonate or organometallic species such as zinc alkyls may be used as catalyst.
(d) polymerization is then conducted at 35° C., without UV light, lasting 24 hours.

EXAMPLE IV

Suspension Polymerization

An example that uses suspension polymerization will now be described.

Modification and Extraction

The enzyme α-chymotrypsin is dissolved in 0.2 M potassium phosphate buffer with a pH of 8.0 and an enzyme concentration of 1–2 mg/ml. The solution is stirred over an ice bath and acryloyl chloride, 175 moles per mole of enzyme, is added periodically over a 20 minute period. The now modified enzyme is separated from excess acryloyl chloride/acrylic acid and buffer salts by passing through a Sephadex G-75 column with 10 mM, pH 7.8 Bis-Tris buffer as the mobile phase. CaCl$_2$ and isopropanol are added to give 2 mM and 1% v/v respectively and excess buffer is added to give an enzyme concentration of 1 mg/ml. The aqueous enzyme solution is brought into contact with an equal volume of isooctane containing 2 mM AOT and stirred for 3 to 5 minutes. The organic phase is removed by centrifugation and the solvent is removed via evaporation in a vacuum oven.

Polymerization

The surfactant-enzyme complex is redissolved in methyl methacrylate to ~10 to 20 mg/ml. The crosslinker, trimethylolpropane trimethacrylate is added to give 5% by wt. Cyclohexane, a nonsolvating diluant, is added at a volume ratio from 0.1:1 to 5:1 solvent:monomer. This is used to impart porosity unto the beads. Other diluents can also be used for such purpose. The initiator, 2,2'-azobis(2,4-dimethyvaleronitrile), is then added at ~1.7 w/v %. The organic phase is then suspended in water containing 0.2% CaCl$_2$. It is assumed that the calcium ions from the CaCl$_2$ bind to any excess AOT (AOT not bound to the enzyme) thus preventing micelles from forming and an emulsion polymerization from occurring. The ratio of organic phase to aqueous phase can range from about 0.05:1 to about 1:1. The suspension is sparged with N$_2$ for 10 seconds and exposed to 365 nm UV radiation while mixing via magnetic stirrer for 12 to 24 hours.

The size and shape of the beads is dependent on the stirring rate, amount of cyclohexane or other solvent, amount and type of suspending agent, and ratio of organic volume to aqueous volume. Beads from ~2 mm to less than 10 μm in diameter have been produced from this method. After the beads have formed they were washed extensively with hexane, dried in a vacuum oven, then washed extensively with water. Finally, the beads are dried in a vacuum oven and stored at room temperature.

Figure 8:
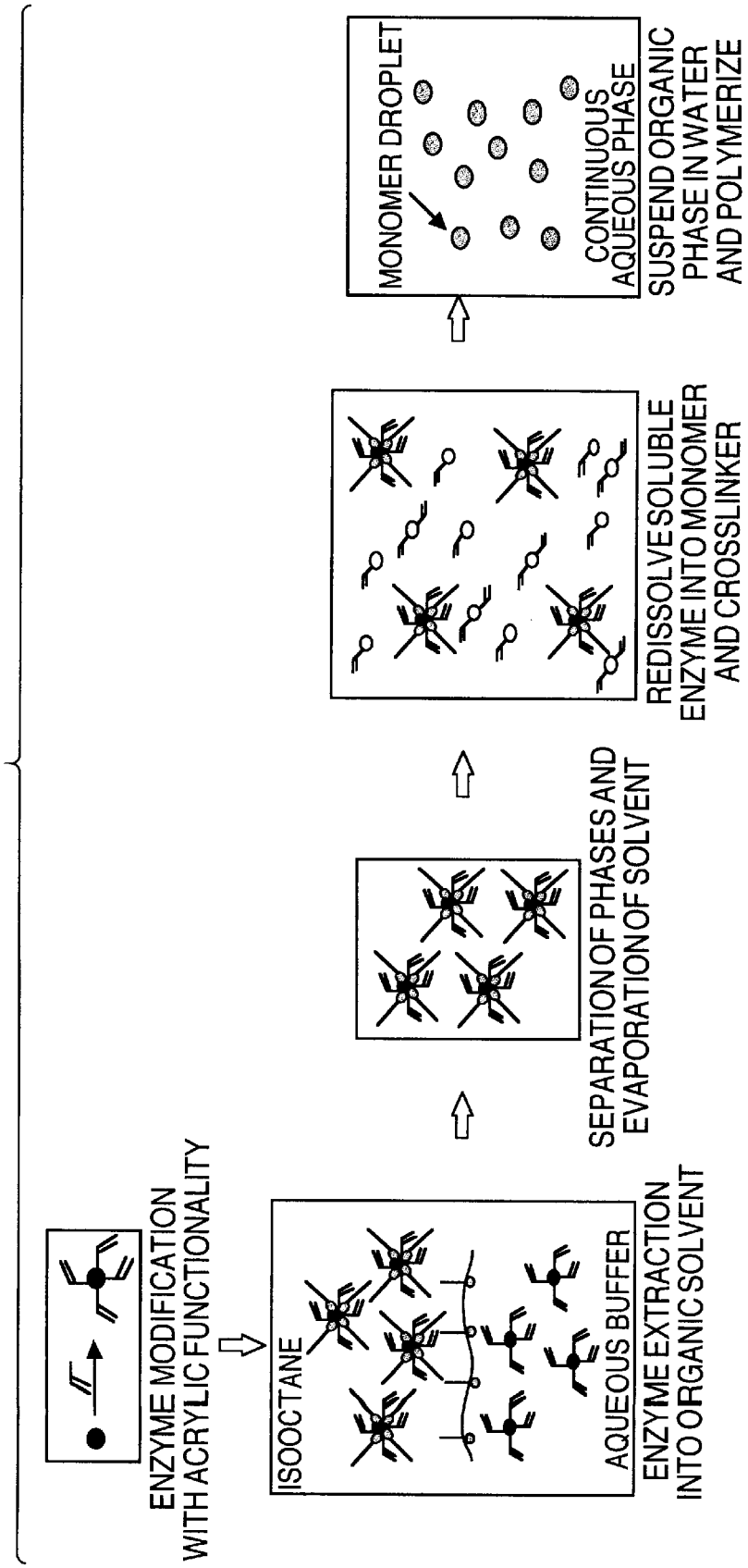
FIG. 8 shows schematically how biocatalytic plastics are produced via suspension polymerization according to the present invention.
Figure 9:
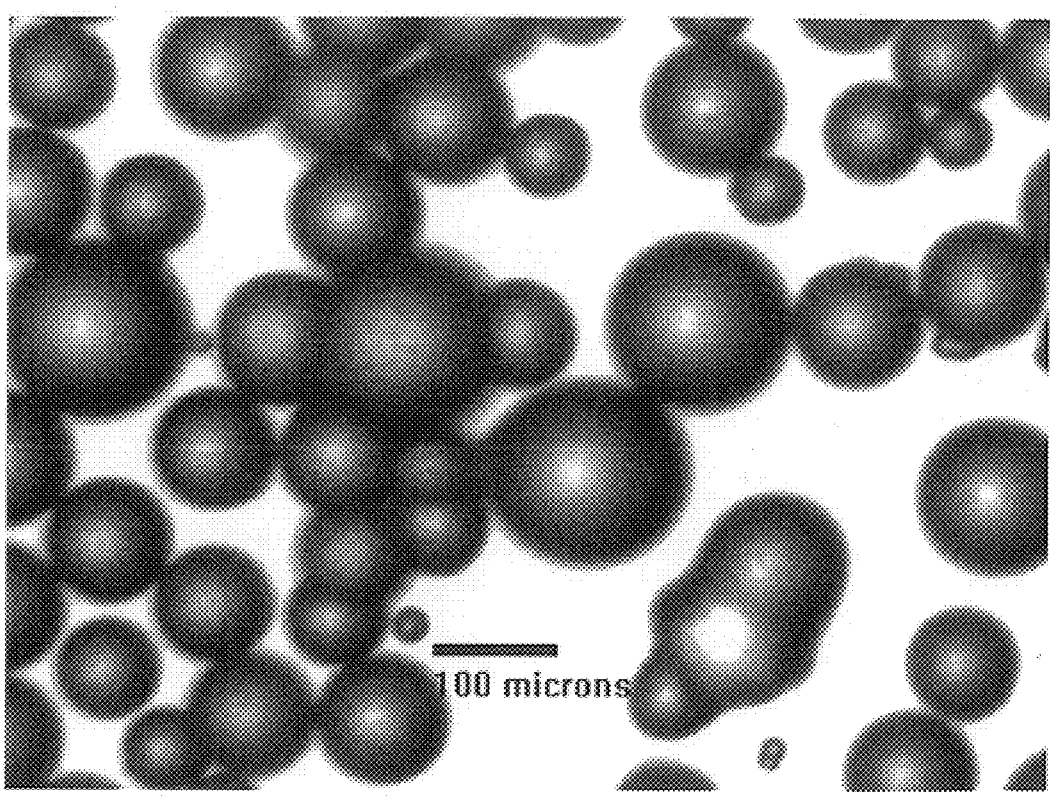
FIG. 9 shows biocatalytic plastic beads produced via suspension polymerization according to the present invention.

Aqueous activity (hydrolysis of N-Succ-AAPF-pNA) of the biocatalytic beads ranges from 0.5 to 5% of the native enzyme. FIG. 8 shows schematically how biocatalytic plastics are produced via suspension polymerization. FIG. 9 shows the resultant beads for the following initial conditions:

Enzyme Extraction 18.2 mg CT modified with 200 molar excess acryloyl chloride extracted into isooctane Organic Phase CT from above MMA: 500 μl TMA: 25 μl
Cyclohexane: 50 μl
Initiator: 10.2 mg
Aqueous Phase
   8 ml of 0.2% $CaCl_2$
Stirring rate
   250 rpm

EXAMPLE V

Emulsion Polymerization

An example that uses emulsion polymerization will now be described.
Modification and Extraction
   This procedure is the same as described above for the suspension polymerization.
Polymerization
   The extracted enzyme from above is dissolved into styrene (or other vinyl monomer) to ~10 mg/ml. The crosslinker, divinyl benzene, is added to give 5% v/v. The initiator, 2,2'-azobis(2,4-dimethyvaleronitrile), is then added to give 2% by volume. This organic phase is then suspended in 15 ml of deionized water, sparged with $N_2$ for 10 seconds and rapidly mixed via a magnetic stirrer. The suspension is exposed to 365 nm UV radiation for 12 to 24 hours to polymerize. It is assumed that the excess AOT not bound to the enzyme forms micelles in which the organic phase is entrapped and polymerizes. The final product is a stable emulsion (latex) which will not settle out with time or with centrifugation and is stored at room temperature.
Actual Synthesis
Modification
   CT: 10 mg
   Buffer: 8 ml 0.2 M, pH 7.8 potassium phosphate buffer
   Acryloyl chloride: 18.1 μl added in 5 25 μl additions of 14.5 μl acryloyl chloride dissolved in 100 μl acetone
      Reaction done over ice bath over a 20 time period
      Enzyme separated in Sephadex G-75 column
Polymerization
   CT: ~4 mg after extraction
   Styrene: 950 μl
   Divinyl benzene: 50 μl
   Initiator: 34 μl of 600 mg/ml in toluene
   Suspended in 15 ml of DI water and rapidly mixed while exposed to UV radiation for 24 hours

EXAMPLE VI

High Enzyme Loading Biocatalytic Plastics
Modification and Extraction
   The enzyme, CT, is dissolved in 0.2 M, pH 7.8 potassium phosphate buffer at a concentration of ~6.7 mg/ml. Acryloyl chloride is added at a 175 molar excess (acryloyl chloride:enzyme) in 5 additions over a 20 minute period while being stirred over an ice bath. After the final addition, the modified enzyme is separated from the unbound acryloyl chloride and buffer salts by passing through a Sephadex G-75 column with a mobile phase consisting of 10 mM Bis-Tris Propane, pH 7.8. Excess buffer with 2 mM $CaCl_2$ and 1% isopropanol is added to give a 1 mg/ml enzyme solution. The aqueous phase is then brought in contact with an equal volume of hexane containing 2 mM AOT. These are mixed together for 3–4 minutes then the organic phase is removed via centrifugation. The hexane is removed by evaporation in a vacuum oven.
Polymerization
   The ion-paired enzyme is then dissolved into an organic phase consisting of 20% MMA, 2% TMA (cross-linker), 1.2% initiator (2,2'-azobis(2,4-dimethyvalero-nitrile)) and the remaining being hexane. Monomer ratios are enzyme:MMA:TMA—1:1:0.05. The solution is sparged with $N_2$ for 10 seconds then exposed to 365 nm UV radiation for 12 to 24 hours to polymerize. The resultant polymer is washed extensively in hexane, dried in vacuum oven, then washed extensively in water. Finally the polymer is dried in a vacuum oven and stored at room temperature. Aqueous activity (hydrolysis of tetrapeptide) is <1% of the native enzyme. Solvent activity for peptide synthesis in isooctane:THF 70:30 (+0.2% water) is ~6 times the suspended native enzyme (this is normalized to enzyme concentration assuming a 50% enzyme loading in the plastic). Activity in hexane for transesterification (APEE and 1-propanol) is ~7 times the suspended native enzyme.
Actual Synthesis
Modification
   CT: 206.5 mg
   Buffer: 30 ml
      Acryloyl chloride: 130.8 μl (175 molar excess) added in 5 additions over 20 minutes
      Reaction done over ice bath, enzyme separated on Sephadex G-75 column.
Extraction
   Buffer: 170 ml Bis Tris Propane, pH 7.8, 2 mM $CaCl_2$, 1% isopropanol
   Organic phase: 200 ml hexane with 2 mM AOT
   Mixed for 4 minutes separated via centrifugation and dried off hexane
Polymerization
   CT: From above (80.4 mg after extraction)
   MMA: 80 μl
   TMA: 8 μl
   Initiator: 8 μl of 600 mg/ml solution in toluene
   Hexane: 300 μl
   The biocatalytic plastics having high loading are especially useful as catalysts for packed bed reactors. Loading of above 10% or even above 50% or even above 80% by weight enzyme are achievable with the present invention.

EXAMPLE VII

Extraction of Proteins with Low pI Values

This method allows utilization of proteins with pI values incompatible with direct ion-pair solubilization in organic solvents and does not require the formation of reversed micelles.

Proteins with low pIs (pI 3–4) possess overall negative charge at physiological pH values (pH 6–7). As a result of this, a preferred surfactant AOT is not very effective for the ion-pairing step because of the repulsive force between the negatively charged protein surface and negatively charged surfactant head groups. For the extraction of low pI enzymes cationic surfactants may be used. In this case positively charged surfactant head groups will be attracted to negatively charged protein surface facilitating ion-pairing.

Another approach involves chemical modification of low pI proteins. generally, prior to extraction with the aim of removing carboxyl groups and/or introducing additional amino groups into the protein molecule (this type of modification is called cationization) . These additional amino groups will increase the pI value of the protein thus allowing high yields of extraction via ion-pairing with AOT at pH values of 7 or 8.

As an example, the enzyme thermolysin (pI about 4) is used. The yield of this enzyme extraction at pH 7.8 using AOT typically does not exceed 5%. The cationization of thermolysin is done in the following way. To 1 mg/ml (30 $\mu$M) thermolysin solution in 0.1 M MES buffer, pH 5 30 mM of 1-ethyl-3-(3-dimethylamino-propyl)carbodiimide and 3 mM of ethylenediamine are added and the mixture is incubated at room temperature under constant agitation for 1 hour. The excess of the reagents is removed by desalting and, simultaneously, the buffer is changed for 10 mM bis-tris propane, pH 7.8. The yield of the extraction of the modified thermolysin into an organic solvent under standard conditions approaches 50%. Thus, the cationization allows the 10-fold increase of the enzyme concentration in the organic solvent.

Other modifications, besides adding amino groups, of low pI proteins may be used so as to increase the pI of the protein. Such modifications can remove the carboxyl groups of the protein by either neutralization or conversion, for example, to amino groups.

Again, the activation achieved in organic solvents by incorporating proteins in plastic matrices according to the present invention allows for the efficient synthesis of peptides, and sugar and nucleoside esters. The polymer-protein composites of the present invention can be used in a variety of applications, including as active and stable biocatalysts in paints, coatings, resins, foams, and beads, as well as membranes, fibers, and tubings.

A common transformation catalyzed by proteins in organic solvents is peptide synthesis. For example, the polymer-protein composites of the present invention, such as a-chymotrypsin (CT)-PMMA composites, are often substantially more effective in catalyzing the peptide synthesis reaction between N-Bz-L-Tyr-Oet and L-Leu-NH$_2$ compared with the lyophilized enzyme suspended in organic solvents. The CT-PMMA material is over 20-fold more reactive than its ion-paired counterpart in isooctane containing 30% v/v THF.

A wide range of tripeptides can be synthesized efficiently using the CP-PMMA material made according to the present invention in comparison with the ion-paired CT. See Table 1. Reaction in more polar solvents, while highly deleterious to the ion-paired CT, if facile for the CT-PMMA biocatalytic plastic. For example, the rate enhancement for CT-PMMA (over the ion-paired enzyme form) in polar organic solvents ranges from about 100 in slightly hydrated ethyl acetate to over three orders of magnitude in acetonitrile (containing 1% v/v, added water).

TABLE 1

Peptide Synthesis by Chymotrypsin-Containing Poly(methyl methacrylate).

| [1] Acyl Donor* | Product | $V_o$ ($\mu$mol (mg E$^{-1}$) (min$^{-1}$)) | | Rate Enhancement $V_{plastic}/V_{ion-paired}$ |
|---|---|---|---|---|
| | | Plastic CT | Ion-paired | |
| Bz-Tyr-OEt[b] | Bz-Tyr-Leu-NH$_2$ | 721 | 35.1 | 20.5 |
| CBZ-Val-Tyr-OEt[b] | CBz-Val-Tyr-Leu-NH$_2$ | 69.0 | 5.61 | 12.3 |
| CBZ-Val-Trp-OEt[b] | CBz-Val-Trp-Leu-NH$_2$ | 46.2 | 0.93 | 49.7 |
| CBZ-Val-Phe-OEt[b] | CBz-Val-Phe-Leu-NH$_2$ | 28.0 | 0.88 | 31.8 |
| CBZ-Val-Leu-OEt[b] | CBz-Val-Leu-Leu-NH$_2$ | 1.95 | 0.081 | 24.1 |
| CBZ-Val-Ala-OEt[b] | CBz-Val-Ala-Leu-NH$_2$ | 1.38 | 0.023 | 60.0 |
| BZ-Tyr-OEt[c] | Bz-Tyr-Leu-NH$_2$ | 35.8 | 0.34 | 105 |
| BZ-Tyr-OEt[d] | Bz-Tyr-Leu-NH$_2$ | 15.9 | 0.085 | 187 |
| BZ-Tyr-OEt[e] | Bz-Tyr-Leu-NH$_2$ | 22.2 | 0.018 | 1230 |

*The acyl acceptor was Leu-NH$_2$ in all cases. The reaction medium contained acyl donor and acceptor concentrations of 5 and 10 mM, respectively, and all amino acids were the natural L isomer. Two milligrams of catalyst were suspended in 2 ml of reaction medium at 30° C. and 250 rpm. The enzyme loading was 0.05 + 0.008% (w/w) in the pMMA.
[b]The solvent was isooctane: THF (7:3, containing 0.2% (v/v) water.
[c]The solvent was ethyl acetate containing 1% (v/v) water.
[d]The solvent was THF containing 1% (v/v) water.
[e]The solvent was acetonitrile containing 1% (v/v) water.

The composites of the present invention can also be used in thymidine acylation, sucrose acylation, and other sugar modifications. For example, one reaction is the subtilisin-catalyzed acylation of sugar-containing compounds such as carbohydrates and nucleosides/deoxy-nucleosides. Thymidine is a moderately good nucleophilic substrate for subtilisin Carlsberg in THF. Thymidine acylation (to the 3'-butyrate derivative) proceeds much more rapidly using subtilisin-PMMA as compared with the ion-paired subtilisin dissolved in the organic solvent. Similarly, acylation of sucrose (to the 1'-butyrate or 1-acrylate derivative) in pyridine proceeded far better with the subtilisin-PMMA than with the ion-paired enzyme form. In both cases, the subtilisin-PMMA also was substantially more reactive than lyophilized, suspended enzyme (up to 540-fold and 210-fold higher for thymidine and sucrose acylation, respectively).

The above described examples of the instant polymer-protein composites, and additional examples, are described in Wang et al., *Nature Biotechnology,* Vol. 15, pp. 789–793, August 1997, which is hereby incorporated by reference in its entirety.

The CT-PMMA, CT-PVA, CT-PST, and CT-PEVE composites of the invention also are highly stable in organic solvent such as hexane and THF. For example, after three weeks, these composites retain full activity in hexane.

The composite of the present invention also have anti-fouling properties and therefore can be used in applications where anti-fouling is desired. If polymeric materials are brought in contact with, for example, a protein solution, protein build-up can develop on the surface of the plastic. This phenomenon (called fouling) hampers the application of polymeric materials, for example, in medicine. Incorporation of one or more enzymes (such as proteases) into plastics according to the present invention helps solve this problem since the low molecular compounds adsorbed on the plastic would be immediately digested by the incorporated enzymes.

α-Chymotrypsin loaded plastics according to the present invention were tested for their anti-fouling properties. As a negative control, an empty (unloaded) plastic was used. Fouling experiments were performed in the following way: 1 mg of plastic was placed in a centrifuge tube, 50 μl of MeOH was added for better suspending of the plastic in the solution. Then 500 μl of 0.1 mg/ml solution of human serum albumin (HSA) was added and the samples were incubated under constant agitation at 30° C. After a certain period of time, plastic was spun down, the HSA solution was removed, the precipitate was briefly washed with water, and the amount of the protein adsorbed on the surface of the plastic was determined using Pierce BCA method. The amount of the protein (enzyme) originally present in the plastic (determined in a similar way but without incubation with HSA solution) was subtracted from the value obtained.

It was found that pMMA that does not contain any enzyme, when incubated in a 0.1 mg/ml human serum albumin solution, accumulates on its surface significant amounts of protein (5–6 μg per 1 mg of plastic) whereas CT-pMMA (10% w/w loading) remains free from protein build-up for more than a week. This shows that μ-chymotrypsin loaded plastics produced according to the present invention posses good anti-fouling properties. Other proteins besides α-chymotrypsin can also be used to give anti-fouling materials.

EXAMPLE VIII

Incorporation of Proteins into Polymeric Materials

The ion-pairing of the protein with a surfactant permits the incorporation of proteins into polymers polymerized prior to the incorporation step. This incorporation can be either (1) physical entrapment, where the protein is not chemically linked to the polymer matrix, or (2) covalent, where the protein is chemically attached to the polymer matrix. During the incorporation, the protein and polymer are both soluble in an organic phase. The protein is solubilized into the organic phase via the formation of hydrophobic ion pairs between the protein and a surfactant. Examples of proteins include those proteins identified herein, such as, subtilisin, thermolysin, pepsin, papain, and antibodies. Examples of polymers include all those identified herein, such as poly(methyl methacrylate), poly(ethyl methacrylate), poly(styrene), poly(vinyl chloride), poly (vinyl acetate) and poly(ethyl vinyl ether).

Entrapment (non-covalent incorporation)

The protein to be incorporated is dissolved in an aqueous buffer at a concentration of about 0.1 to 10 mg/ml, preferably about 1 mg/ml. When incorporating enzymes, the pH of the buffer is preferably at or near the pH at which the enzyme has maximal activity. An immiscible organic phase of about the same volume, containing a surfactant, such as AOT, at a concentration below that required for the formation reverse micelles (for example, 2 mM), is brought into contact with the aqueous phase and thoroughly mixed.

Figure 10:
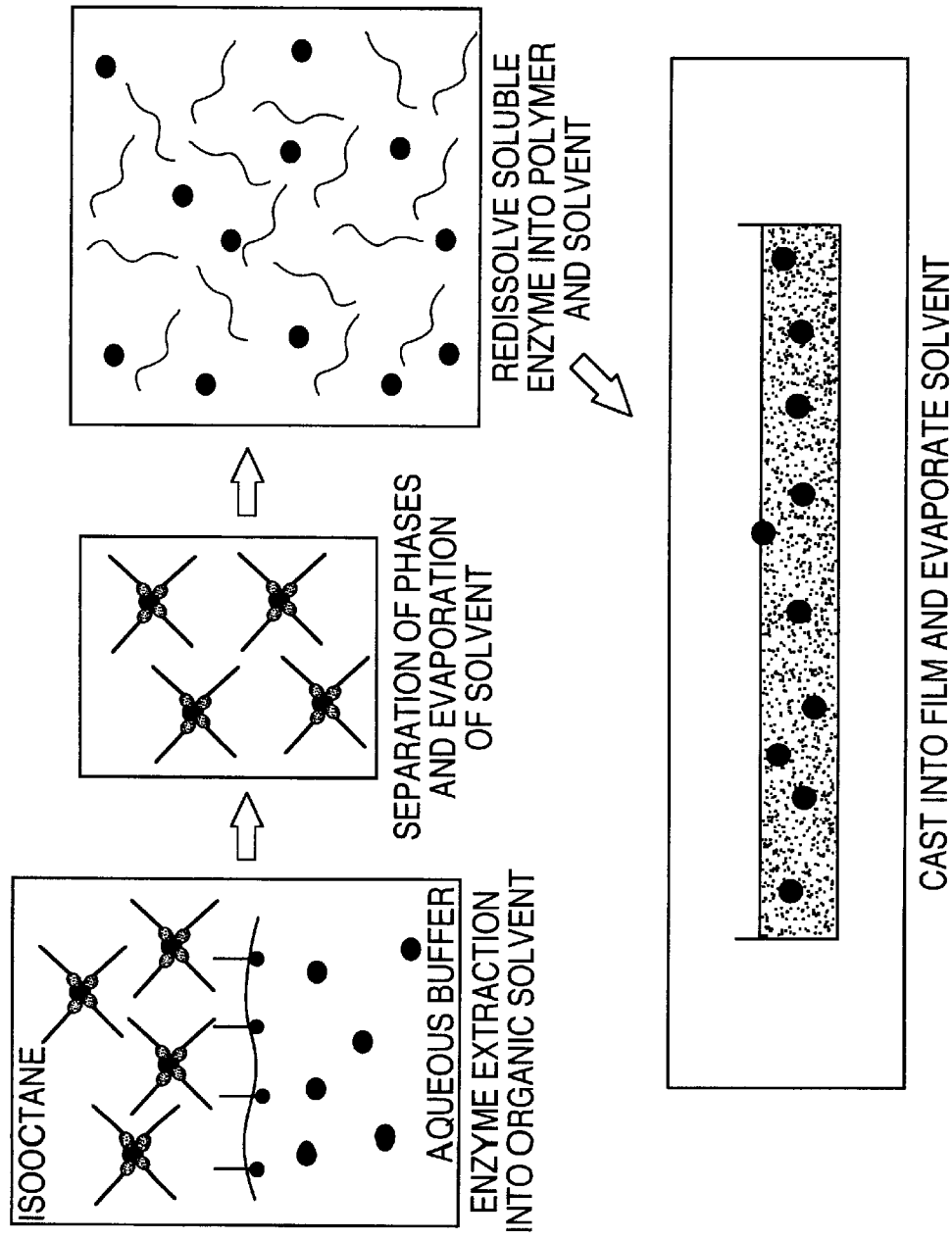
FIG. 10 is a schematic diagram depicting the incorporation of a protein into a polymeric material.

After about 3 minutes, the two phases are separated via centrifugation. The organic phase containing the ion paired protein is separated from the aqueous phase and dried until no solvent remains. The ion paired enzyme is redissolved into a solvent which the polymer is also soluble in, such as toluene. The polymer, dissolved in the same solvent as the protein (at a concentration of about 0.1 to 10 w/v%, preferably 5 w/v%), is added to the ion paired protein solution and gently mixed. The protein-polymer solution can either be poured out into a dish and the solvent can be removed by evaporation under a vacuum or the protein-polymer complex can be precipitated out by the addition of a non-solvent (a solvent which the polymer is not soluble in) such as hexane. A schematic diagram of this approach can be found in FIG. 10.

Covalent incorporation

The extraction of the protein is the same as described immediately above. The dried ion paired protein is then dissolved into a solvent that the polymer is also soluble in. In this case, the overall schematic of FIG. 10 still holds true except that in addition the polymer contains reactive functional groups. These groups can be carboxylic acids, alcohols, amino groups, or any other suitable reactive group. These groups are incorporated into the polymer either by copolymerization with the appropriate monomer or by post-polymerization modification of the polymer. After mixing of the protein and polymer, the two are allowed to react and covalently bind together. Activating agents, such as carbodiimides, may be added if necessary. The protein-polymer complex can either be dried in under a vacuum or precipitated in a nonsolvent.

Figure 11:
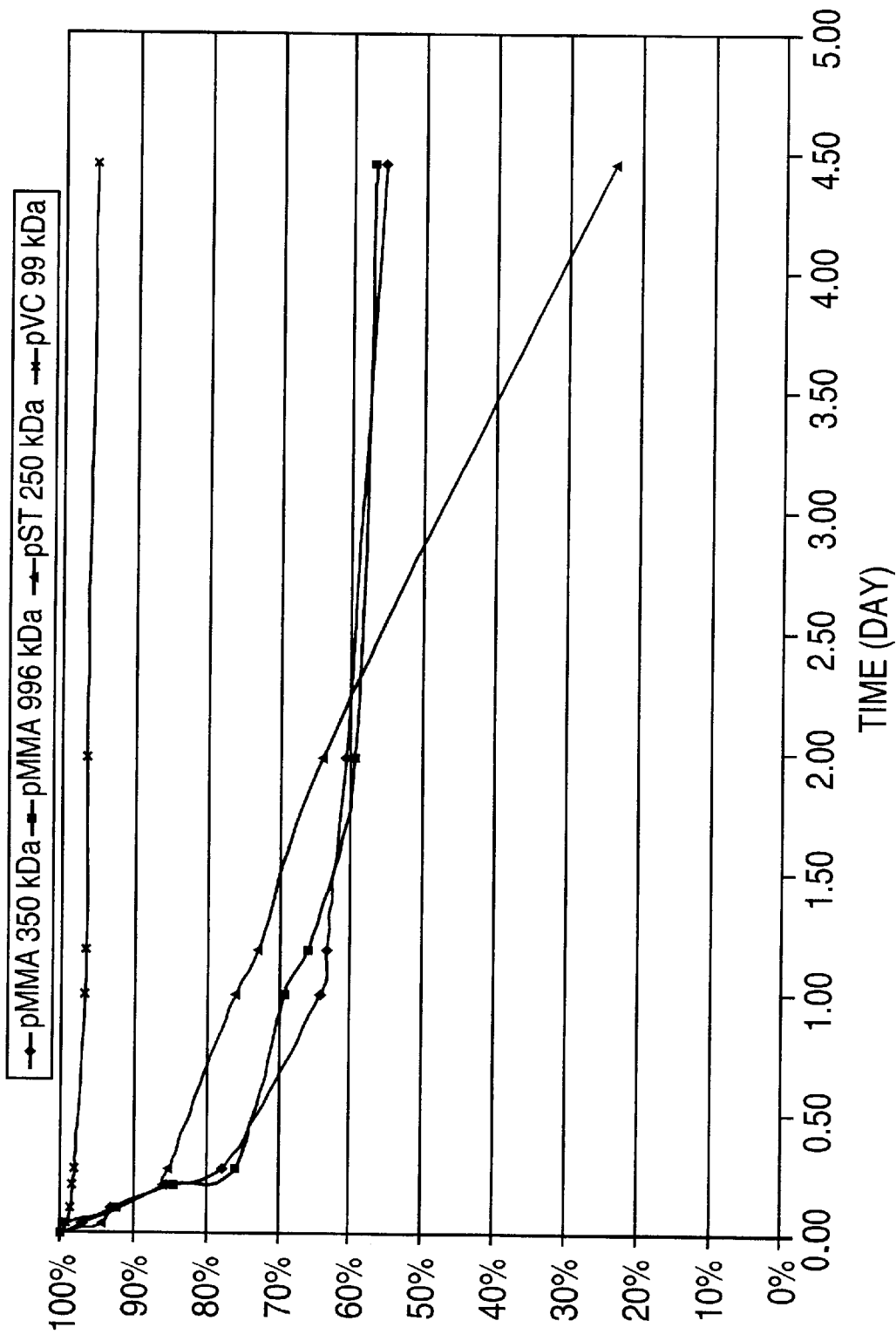
FIG. 11 is graph depicting the amount of chymotrypsin remaining in a composition according to the invention after incubation in water.
Figure 12:
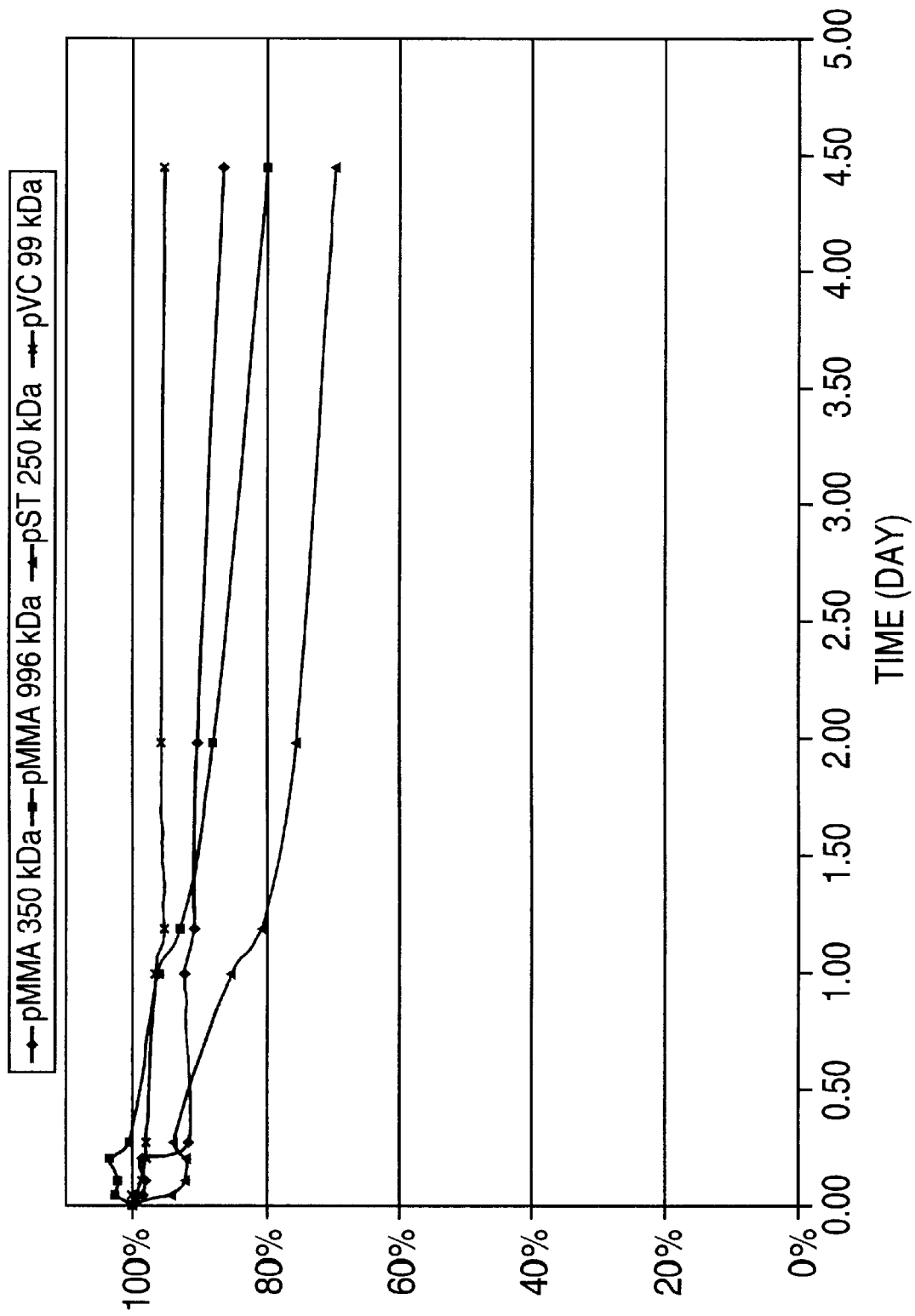
FIG. 12 is graph depicting the amount of chymotrypsin remaining in a composition according to the invention after incubation in hexane.

The noncovalent method achieved the following. The leaching of protein from a noncovalently entrapped protein-polymer complex is shown in FIGS. 11 and 12. This was measured by punching out discs of 1.6 cm in diameter from a protein-polymer film and incubating them in either 5 ml of water or hexane. The absorbance at 280 nm of the supernatant was measured at various time intervals to determine how much protein leaches from the protein-polymer film. This was done using α-chymotrypsin and four polymers: poly(methyl methacrylate) at 350 and 996 kDa, poly (styrene) at 250 kDa, and polylvinyl chloride) at 99 kDa.

The activity of the enzyme-polymer complexes was measured by determining the initial rate of conversion of N-acetyl-phe-ethyl ester with n-propanol in hexane. Substrate and product concentrations were determined using gas chromatography. Enzyme-polymer discs of 0.8 cm in diameter were incubated in the substrate solution (1.8 ml) and periodically 110 μl of the solution was removed and analyzed. The activity is given in Table 2 below

| Polymer | Activity (μmol/hr · mg total) |
| --- | --- |
| p(methyl methacrylate) - 350 kDa | 0.391 |
| p(methyl methacrylate) - 996 kDa | 0.256 |
| p(styrene) - 250 kDa | 0.289 |

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein.

What is claimed is:

1. A method of preparing a polymer-protein composite comprising
   ion-pairing a protein in an aqueous phase with a surfactant in a first organic phase to yield a protein-surfactant ion pair;
   contacting the protein-surfactant ion pair with a second organic phase containing at least one selected from the group consisting of the polymer or a monomer that can be polymerized to yield the polymer;
   removing the second organic phase to yield a polymer-protein composite.

2. The method according to claim 1, wherein the second organic phase comprises the monomer.

3. The method according to claim 2, wherein the monomer is polymerized by suspension polymerization.

4. The method according to claim 2, wherein the monomer is polymerized by emulsion polymerization.

5. The method according to claim 1, wherein the second organic phase comprises the polymer.

6. The method according to claim 5, wherein the protein is modified chemically with one or more reactive functional groups that can form a covalent bond with the polymer.

7. The method according to claim 1, wherein the protein is a naturally-occurring protein.

8. The method according to claim 1, wherein the polymer-protein composite comprises from 0.05% to 90% by weight of protein, based on the total weight of the composite.

9. The method according to claim 6, wherein the reactive functional group comprises a vinyl group.

10. The method according to claim 6, wherein the reactive functional group comprises an acrylate group.

11. The method according to claim 1, wherein the protein is an enzyme.

12. A method of preparing a polymer-protein composite that comprises
   (a) contacting and mixing a protein-containing aqueous solution with a surfactant in an organic solution to yield an organic phase containing an protein-surfactant ion pair,
   (b) separating out the organic phase that contains the ion pair from the aqueous phase that no longer contains the ion pair,
   (c) removing the organic solution from the organic phase of (b),
   (d) dissolving the ion-pair in a second organic solution,
   (e) contacting the dissolved ion-pair of (d) with a polymer that is also dissolved in the second organic solution to form a polymer-protein complex and
   (f) recovering the polymer-protein complex.

13. The method according to claim 12, wherein the protein is modified chemically with one or more reactive functional groups that can form a covalent bond with the polymer.

14. The method according to claim 12, wherein the protein is a naturally-occurring protein.

15. The method according to claim 12, wherein the polymer-protein composite comprises from 0.05% to 90% by weight of protein, based on the total weight of the composite.

16. The method according to claim 13, wherein the reactive functional group comprises a vinyl group.

17. The method according to claim 13 wherein the reactive functional group comprises an acrylate group.

18. The method according to claim 12, wherein the protein is an enzyme.

19. A polymer-protein composite comprising a protein incorporated in a polymer,
   wherein the polymer-protein composite comprises from about 0.05 to 90% by weight of protein, based on the total weight of the composite,
   wherein the polymer-protein composite is obtainable by:
   ion-pairing of a protein in an aqueous phase with a surfactant in a first organic phase to yield a protein-surfactant ion pair;
   contacting the protein-surfactant ion pair with a second organic phase containing at least one selected from the group consisting of the polymer or a monomer that can be polymerized to yield the polymer;
   removing the second organic phase to yield a polymer-protein composite.

20. The polymer-protein composite according to claim 19, wherein the protein is covalently bound to the polymer.

21. A polymer-protein composite comprising a protein incorporated in a polymer,
   wherein the polymer-protein composite comprises from about 0.05% to 90% by weight of protein, based on the total weight of the composite,
   wherein the polymer-protein composite is obtainable by
   (a) contacting and mixing a protein-containing aqueous solution with a surfactant in an organic solution to yield an organic phase containing an protein-surfactant ion pair,
   (b) separating out the organic phase that contains the ion pair from the aqueous phase that no longer contains the ion pair,
   (c) removing the organic solution from the organic phase of (b),
   (d) dissolving the ion-pair in a second organic solution,
   (e) contacting the dissolved ion-pair of (d) with a polymer that also is dissolved in the second organic solution to form a polymer-protein complex and
   (f) recovering the polymer-protein complex.

22. The polymer-protein composite according to claim 21, wherein the protein is covalently bound to the polymer.

23. The method according to claim 12, wherein the polymer is formed from a monomer that is polymerized by suspension polymerization.

24. The method according to claim 12, wherein the polymer is formed from a monomer that is polymerized by emulsion polymerization.

25. The method according to claim 19, wherein the monomer is polymerized by suspension polymerization.

26. The method according to claim 19, wherein the monomer is polymerized by emulsion polymerization.

27. The method according to claim 21, wherein the polymer is formed from a monomer that is polymerized by suspension polymerization.

28. The method according to claim 21, wherein the polymer is formed from a monomer that is polymerized by emulsion polymerization.

* * * * *

UNITED STATES PATENT AND TRADEMARK OFFICE
CERTIFICATE OF CORRECTION

PATENT NO. : 6,291,582 B1
DATED : September 18, 2001
INVENTOR(S) : Dorkick et al.

It is certified that error appears in the above-identified patent and that said Letters Patent is hereby corrected as shown below:

<u>Title page,</u>
Item [73], Assignee, add -- University of Iowa Research Foundation --

Signed and Sealed this

Eleventh Day of November, 2003

JAMES E. ROGAN
*Director of the United States Patent and Trademark Office*